(12) United States Patent
Fichera

(10) Patent No.: US 7,514,044 B2
(45) Date of Patent: Apr. 7, 2009

(54) VIAL PRESENTATION MODULE, SLIDE DISPENSER AND SLIDE PRESENTATION MODULE

(75) Inventor: Stephen L. Fichera, Salem, NH (US)

(73) Assignee: Cytyc Corporation, Marlborough, MA (US)

( * ) Notice: Subject to any disclaimer, the term of this patent is extended or adjusted under 35 U.S.C. 154(b) by 806 days.

(21) Appl. No.: 10/998,029

(22) Filed: Nov. 24, 2004

(65) Prior Publication Data

US 2006/0110293 A1 May 25, 2006

(51) Int. Cl.
*B01L 3/00* (2006.01)
(52) U.S. Cl. ...................................... 422/99
(58) Field of Classification Search ................ 422/99
See application file for complete search history.

(56) References Cited

U.S. PATENT DOCUMENTS

| | | | |
|---|---|---|---|
| 2,649,093 A | 8/1953 | Rigney | |
| 2,896,821 A | 7/1959 | Stegeman | |
| 3,235,068 A | 2/1966 | Asnes et al. | |
| 3,393,831 A | 7/1968 | Stewart | |
| 3,459,297 A | 8/1969 | Templeton et al. | |
| 3,930,928 A | 1/1976 | Tapert | |
| 4,018,643 A | 4/1977 | Levine | |
| 4,801,431 A | 1/1989 | Cuomo et al. | |
| 4,817,820 A | 4/1989 | Heiland | |
| 4,838,423 A | 6/1989 | Lerner et al. | |
| 5,075,079 A | 12/1991 | Kerr et al. | |
| 5,208,762 A | 5/1993 | Charhut et al. | |
| 5,366,896 A | 11/1994 | Margrey et al. | |
| 5,383,569 A | 1/1995 | Muto | |
| 5,975,349 A | 11/1999 | Menes | |
| 6,020,995 A | 2/2000 | Dreyer et al. | |
| 6,093,574 A | 7/2000 | Druyor-Sanchez et al. | |
| 6,135,314 A | 10/2000 | Menes | |
| 6,256,967 B1 | 7/2001 | Hebron et al. | |
| 6,317,648 B1 | 11/2001 | Sleep et al. | |
| 6,382,460 B1 | 5/2002 | González | |
| RE37,829 E | 9/2002 | Charhut et al. | |
| 6,449,927 B2 | 9/2002 | Hebron et al. | |
| 6,522,945 B2 | 2/2003 | Sleep et al. | |

(Continued)

*Primary Examiner*—Walter D Griffin
*Assistant Examiner*—Bobby Ramdhanie
(74) *Attorney, Agent, or Firm*—Vista IP Law Group LLP

(57) ABSTRACT

An apparatus for uncapping and capping a vial while maintaining a relationship between a cap and a particular vial includes rotatable members, the rotation of which is coordinated so that the first and second members assume at least two common positions, and a capped vial is loaded into the first member and a cap is removed from the vial and held by the second member while the rotatable members are in a common position. The cap is applied to the vial by the second member while in the members are in a second common position. An apparatus for storing and dispensing slides includes a cartridge that holds slides that are horizontally stacked on a bottom surface of the cartridge. The slides stand up at least partially on one side and are dispensed from the cartridge through a recess in the bottom of the cartridge. An apparatus for storing and presenting slides includes a cartridge having a slot, a shaft with trays extending there from, a motor for rotating the shaft and an actuator. The actuator contacts a slide on a tray and displaces the slide from an original position on the tray inside the cartridge to an extended position through the slot at least partially outside of the cartridge.

13 Claims, 21 Drawing Sheets

U.S. PATENT DOCUMENTS

| | | |
|---|---|---|
| 6,582,962 B1 | 6/2003 | Richards et al. |
| 6,697,149 B2 | 2/2004 | Baer et al. |
| 6,742,671 B2 | 6/2004 | Hebron et al. |
| 2002/0001074 A1 | 1/2002 | Baer et al. |
| 2002/0079239 A1 | 6/2002 | Hrisinko |
| 2004/0072225 A1 | 4/2004 | Rollins et al. |

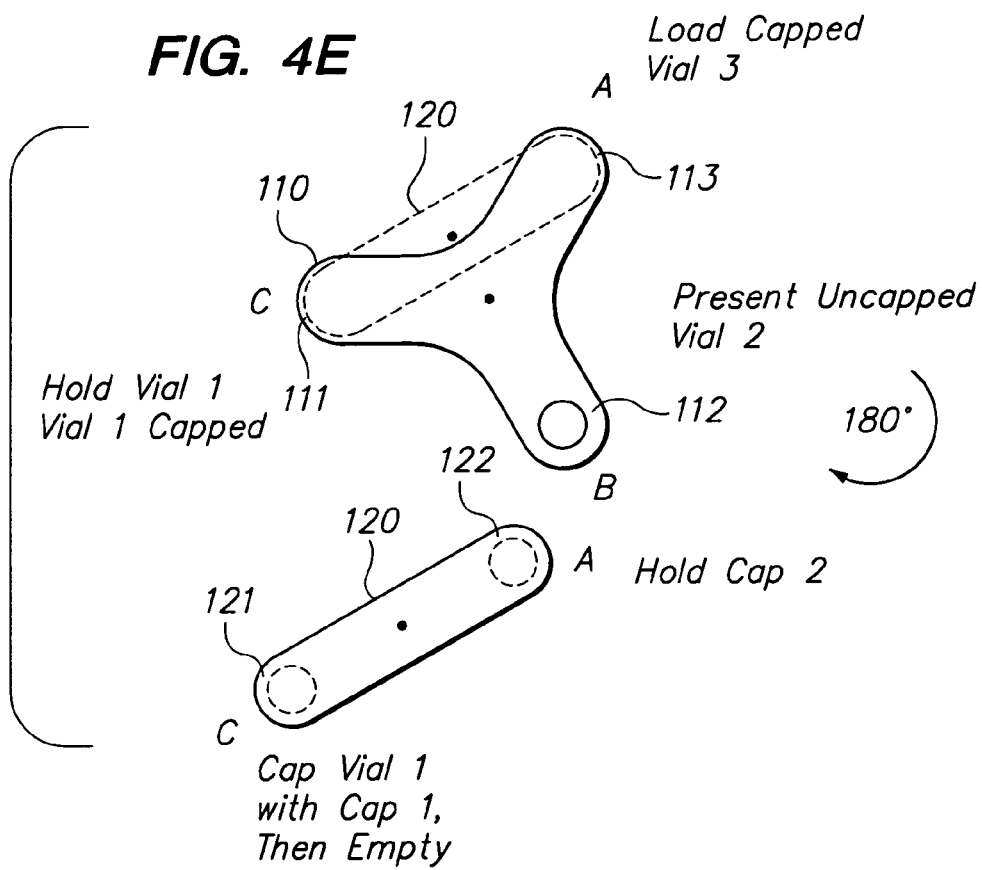
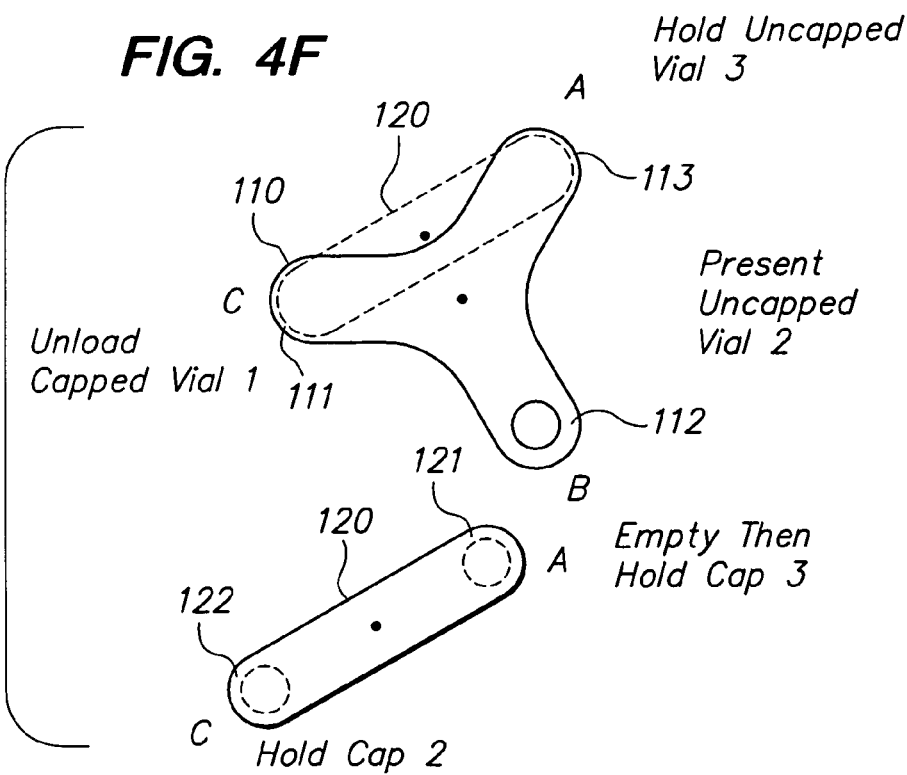

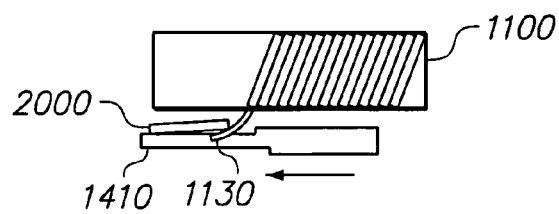
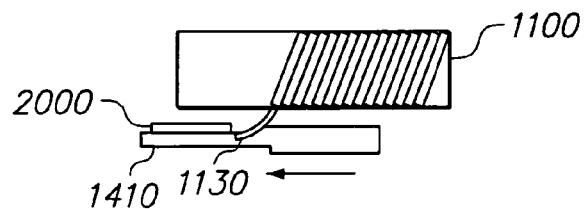
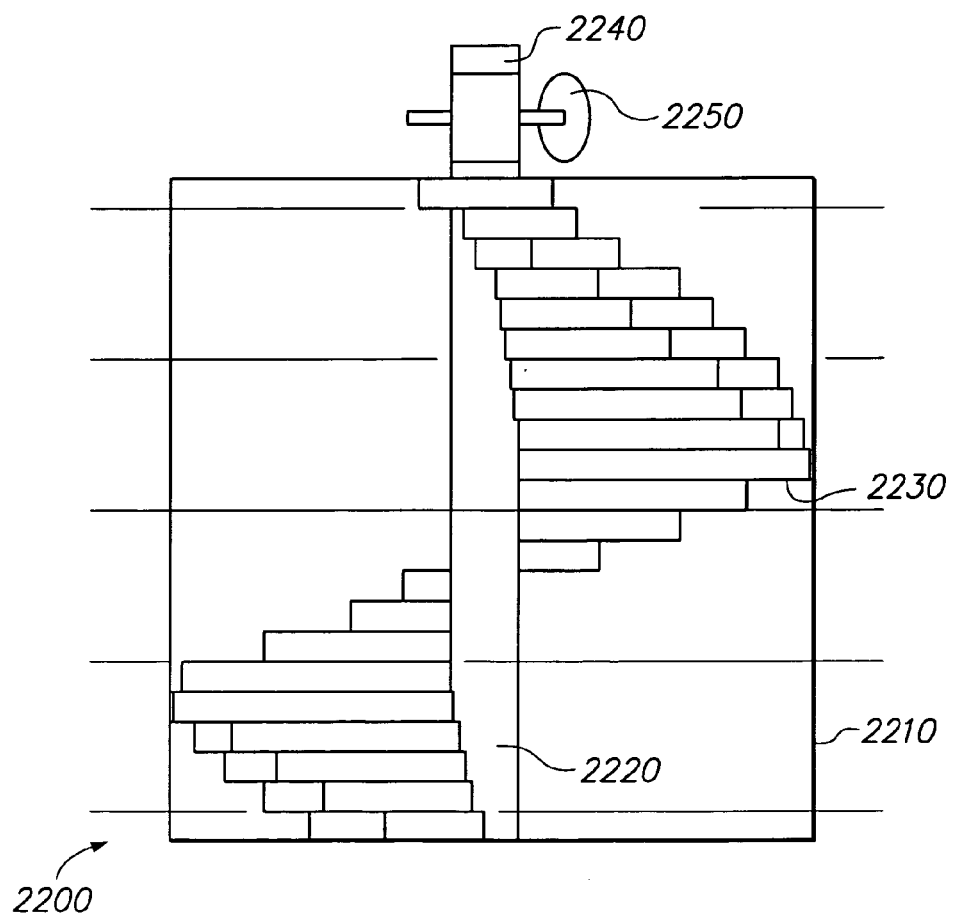

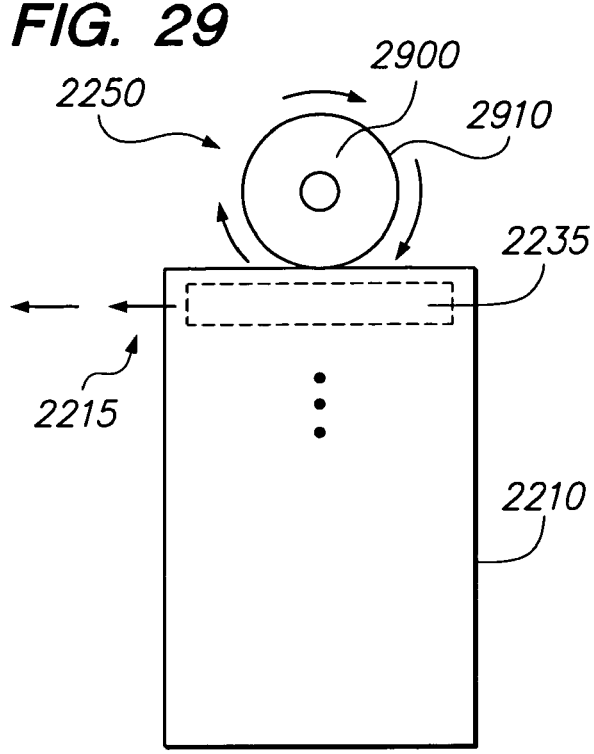
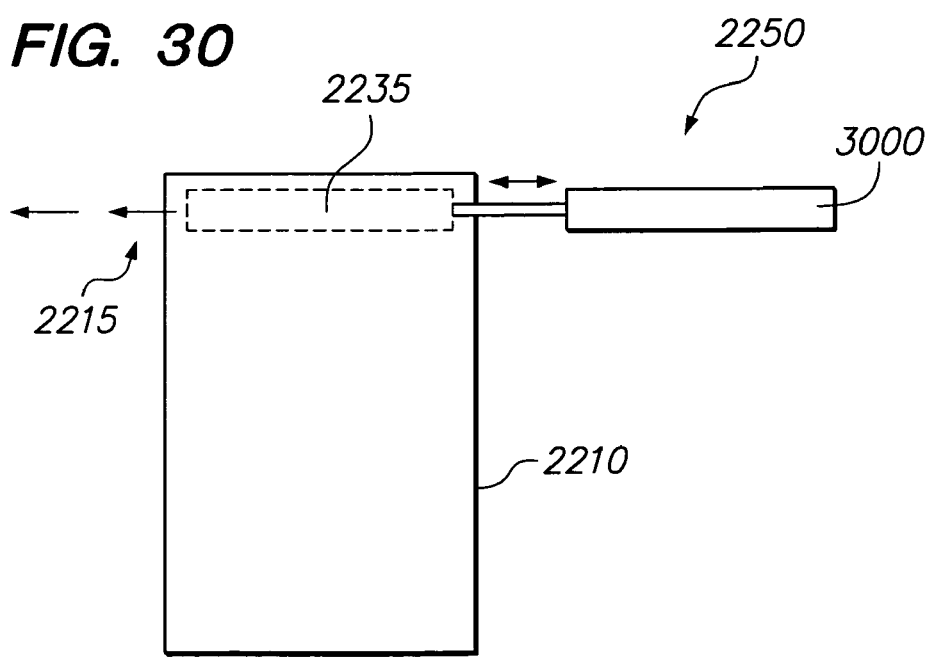

VIAL PRESENTATION MODULE, SLIDE DISPENSER AND SLIDE PRESENTATION MODULE

FIELD OF THE INVENTION

Embodiments relate to equipment used in the preparation of biological specimen slides and, more particularly, to a module that automatically uncaps, presents and caps vials, a slide dispensing apparatus that arranges slides on a side rather than being stacked vertically one on top of another, and a module that presents a slide from a top of a cartridge that includes a fanning or helical arrangement of trays and slides.

BACKGROUND

Medical professionals and technicians, such as cytotechnologists, prepare numerous slides with samples of biological specimens. A cytotechnologist retrieves a vial or container having a sample, removes the cap or cover from the vial, obtains a sample, places a sample on a slide, places the cap back on the vial to close the vial, and places the vial back in a rack or storage. A cytotechnologist typically uses a marker to label the cap to identify which cap belongs to a particular vial so that the wrong cap is not placed on the wrong vial this prevents cross-contamination of samples in different vials. Repeating these manual uncapping, marking and capping actions to prepare multiple specimen slides is very time consuming, inefficient, and labor intensive. A cytotechnologist's valuable time that is wasted with these tasks would be better spent analyzing specimen samples and conducting other more important work.

Some known systems have provided for machines having limited capping functionality or limited de-capping functionality, particularly in the area of filling and capping vials that are filled with prescription drugs. Known systems, however, can be improved. For example, a system should be automated so that a vial can be automatically loaded, uncapped, presented to a cytotechnologist or processing device to obtain a sample, and automatically re-capped. An automated system should eliminate many of the tedious and repetitive uncapping, marking and capping tasks that are associated with known systems and techniques. In addition, automated systems should place the correct cap on a particular vial so that samples are not contaminated or misidentified.

Cytotechnologists may also utilize slide cartridges for storing and dispensing slides. Cartridges typically store slides in a vertically stacked arrangement. For example, some cartridges store about 100 to 200 slides, one on top of another, so that, top to bottom surfaces of adjacent slides are in contact with each other. A stack of about 100 glass slides can impart a force of about one pound on the bottom glass slide. Such forces can present significant problems for processing machines and devices that retrieve a bottom slide from the stack and deliver the selected slide to another processing station for applying a specimen sample, staining, printing, etc. For example, a machine or device may have difficulty pushing a slide out from underneath the stack of other slides as a result of the weight and friction on the top surface of the bottom slide caused by the weight of the slides above. A machine or device may also accidentally select more than one slide as a result of slides being arranged in a vertical stack and the selection element not being able to engage an individual slide. Further, a slide may also "tiddlywink" or flop upward at an angle or exhibit other irregular motions as the slide is close to being pushed out from underneath the stack of slides. These irregular motions result from the weight of the slides above being focused on the second or last end of the slide as the last end is removed from underneath the stack. These irregular motions can result in slide placement errors and damaged slides.

Known slide cartridges can thus be improved. Slides should be arranged within and dispensed from a cartridge in a more reliable and predictable manner. The vertical weight that is applied to individual slides, in particular, to ends of slides as they are pushed out from underneath a stack of slides, should be reduced and/or eliminated. Slides should also be dispensed from a cartridge to a predictable position that enables a cytotechnologist or a processing device or machine to easily select the dispensed slide, thus reducing slide picking and processing errors.

SUMMARY

According to one embodiment, an apparatus for uncapping and capping a vial while maintaining a relationship between a cap and a particular vial includes first and second rotatable members. The first rotatable member can holds a vial in a plurality of positions. The second member can uncap and cap a vial. The first and second members are rotated in a coordinated manner so that the first and second members assume at least two common positions. In one common position, a capped vial is loaded into the first member and a cap being removed from the vial and held by the second member. In the second common position, the cap is applied to the vial by the second member.

The second member can rotate above the first member. The members can have lobes. The members can have the same number of lobes, or a different number of lobes, e.g., one member can have two lobes and the other can have three lobes. The The first member is rotatable among positions for loading and uncapping a vial, presenting the opened vial, and capping and unloading a vial. The second member can uncap a vial and hold the cap. The members can rotate around a common or different axis depending on the configuration of the members and thus, can rotate a different number of degrees between different stations or stops.

According to another embodiment, an apparatus for storing and dispensing slides includes a cartridge that is configured to hold a plurality of slides that are horizontally stacked on a bottom surface of the cartridge so that the slides stand up at least partially on one side. The bottom of the cartridge includes a recess, and a slide is dispensed from the cartridge through the recess.

Thus, none of the slides are stacked vertically or on a top or bottom surface within the cartridge, and gravity is the primary vertical force that is applied to an individual slide within the cartridge and that causes a slide to be dispensed from the cartridge through the recess. The slides can be arranged inside the cartridge so that each slide stands up on one side or at an angle, for example, 45-90 degrees with respect to the bottom surface of the cartridge, and a slide can be dispensed through the recess at angle of about 10-45 degrees with respect to the bottom surface of the cartridge. A slide can be dispensed from the cartridge onto a holding member, such as a pair of ramp members or a belt, and the slide comes to rest on the holding member and can be retrieved or selected by processing equipment.

According to a further embodiment, an apparatus for storing and presenting slides includes a cartridge that has a slot, a shaft, trays that extend from the shaft and that are for holding a slide, a motor that rotates the shaft and an actuator. The actuator contacting a slide on a tray, displacing the contacted slide from an original position on the tray inside the cartridge to an extended position through the slot and at least partially outside of the cartridge.

The trays can be radially and vertically offset from each other and arranged in, for example, a fanning or helical arrangement along the shaft. The actuator can be a wheel, such as a friction wheel or a reciprocating member, which displaces the slide partially outside of the cartridge or ejects the slide from the cartridge. The shaft can be rotated to position the next slide into a position to be displaced or ejected, e.g., in a stepwise manner or for a certain number of degrees depending on the number of trays extending from the shaft.

BRIEF DESCRIPTION OF THE DRAWINGS

Referring now to the drawings in which like reference numbers represent corresponding parts throughout:

FIGS. 4A-H illustrate different positions of a vial holding member and an uncapping/capping member during phases of automated vial uncapping and capping;

FIGS. 21A-G illustrate how slides that are stacked at least partially on one side are dispensed from a cartridge and onto fingers of a slide platform having a friction surface or pad;

FIG. 22 is a partial side view of a cartridge having trays that that hold slides in a spiral or helical arrangement;

FIG. 29 illustrates a friction wheel actuator according to one embodiment; and

FIG. 30 illustrates a reciprocating actuator according to another embodiment.

DETAILED DESCRIPTION OF ILLUSTRATED EMBODIMENTS

In the following description, reference is made to the accompanying drawings which form a part hereof, and which show by way of illustration specific embodiments in which embodiments may be practiced. It is to be understood that structural changes may be made without departing from the scope of embodiments.

Referring to FIGS. 1A-3B, one embodiment provides an apparatus 100 for uncapping and capping a vial while maintaining a relationship between a cap that is associated with a particular vial. The apparatus includes a first rotatable vial holding member 110 and a second rotatable uncapping/capping member 120.

Figure 1A:
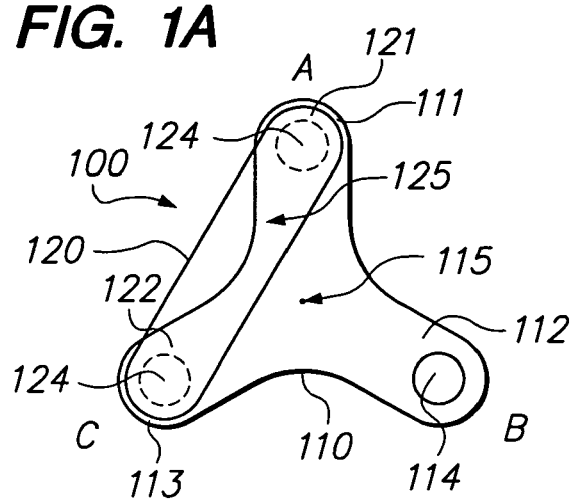
FIGS. 1A-B are respective top and side views of a two-lobe uncapping/capping member and a three-lobe vial holding member according to one embodiment.
Figure 1B:
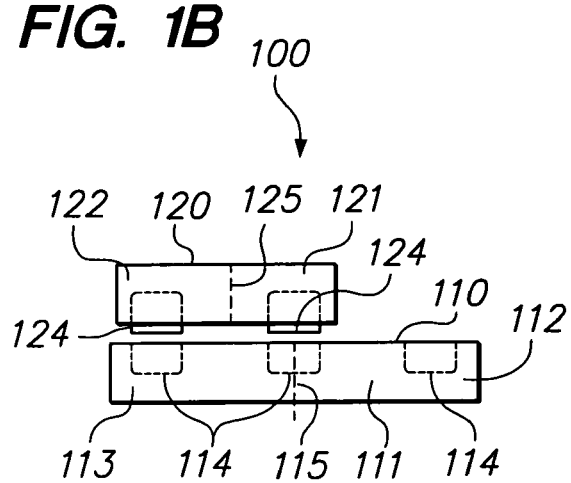
Figure 1C:
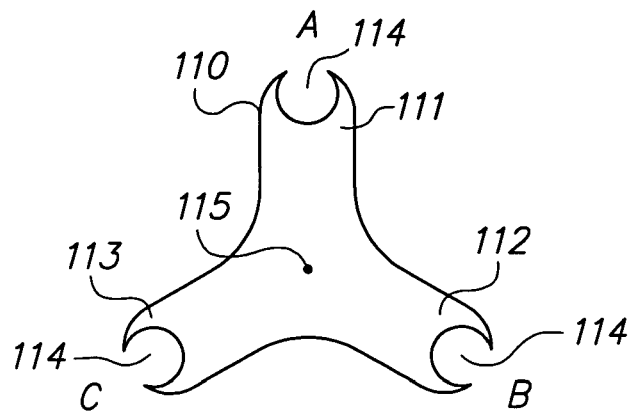
FIG. 1C illustrates an alternative embodiment of a three-lobe member for holding a vial.
Figure 2A:
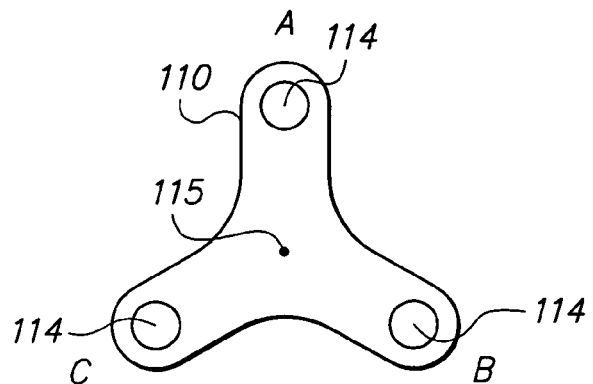
FIGS. 2A-B are respective top and side views of a three-lobe member for holding a vial in a plurality of positions according to one embodiment.
Figure 2B:
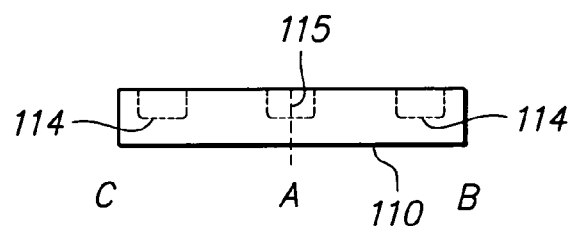
Figure 3A:
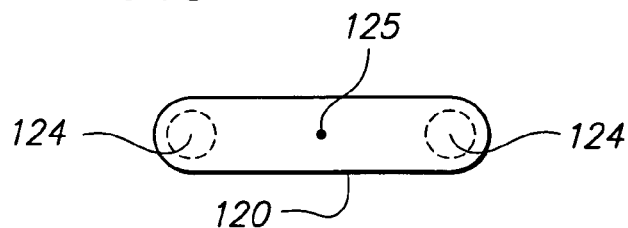
FIGS. 3A-B are respective top and side views of a two-lobe member for uncapping and capping a vial according to one embodiment.
Figure 3B:
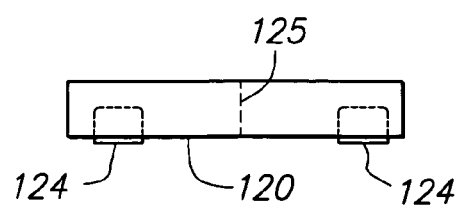

In the embodiment shown in FIGS. 1A-3B, the first rotatable member 110 has a generally triangular shape having three lobes 111-113. The second rotatable member 120 is a two-lobe member having lobes 121 and 122. The lobes 111-113 of the first member 110 include mechanisms 114 that are used to hold or secure a vial. The holding mechanism 114 can be, for example, cavities formed within a top surface of the first rotatable member 110 as shown in FIGS. 1A-B and 2.

Alternatively, the holding members 114 can be flexible finger-like retaining members that wrap around a vial, as shown in FIG. 1C. A vial can be secured between the finger-like members and removed from the members by hand or by another processing machine or device. For purposes of illustration and explanation, this specification primarily refers to the holding members 114 shown in FIGS. 1A-B and 2.

The lobes 121 and 122 of the second rotatable member 120 include uncapping/capping mechanisms or "spinner" mechanisms 124. A spinner mechanism 124 grasps or latches onto a cap and rotates the cap in a clockwise or counterclockwise direction. The mechanism 124 rotates in one direction to remove the cap from the vial and holds the cap after it is removed. The mechanism 124 reapplies the cap that it holds to a vial, preferably the vial that is associated with that particular cap, by rotating the cap in an opposite direction to screw the cap back onto the vial. Persons skilled in the art will recognize that other decapping/capping mechanisms 124 other than "spinner" mechanisms that rotate caps from and onto threaded vials can be used. For example, the cap may instead be removed by lifting the cap from a vial by overcoming a sealing pressure rather than unscrewing the cap. The uncapping/decapping mechanism 124 can be configured as needed depending on the capping method used.

The first and second members 110 and 120 rotate about respective axes 115 and 125, and the second rotatable member 120 rotates above the first rotatable member 110. In the illustrated embodiment, the first and second members 110 and 120 rotate about different axes 115 and 125. In other words, the first member 110 rotates about a central axis 115, and the second member 120 rotates about an axis 125 that is offset relative to the central axis 115.

In the illustrated embodiment, the first member 110 rotates among three different positions A, B and C. Position A is generally referred to as the "loading/uncapping" position. In this position, a capped vial is loaded from a cartridge or other source and into a lobe of the first member 110. The cap is removed from the loaded vial. Position B is generally referred to as the "presentation" position. In this position, an uncapped vial is presented or provided to a cytotechnologist so that a specimen sample can be obtained from the uncapped vial. Position C is generally referred to as the "capping/unloading" position. In this position, the vial is recapped with the same cap, and can be unloaded from the lobe of the first member 110.

In the illustrated embodiment, the second member 120 rotates between two positions. With its uncapping and capping functions, the second member 120 rotates between at least the "loading/uncapping" position A and the "capping/unloading" position C. Rotation of the first and second members 110 and 120 is coordinated to provide automated uncapping and capping of vials is described in further detail below, with reference to FIGS. 4A-H and 5.

FIGS. 4A-H illustrate the different positions of the first member 110 and the second member 120 and the associated uncapping, presentation and re-capping stages. In the top portion of each of FIGS. 4A-H, the second member 120 is shown in phantom so that the first member 110 can be clearly seen, and the second member 120 is shown in full there below relative to the first member 110.

Figure 4A:
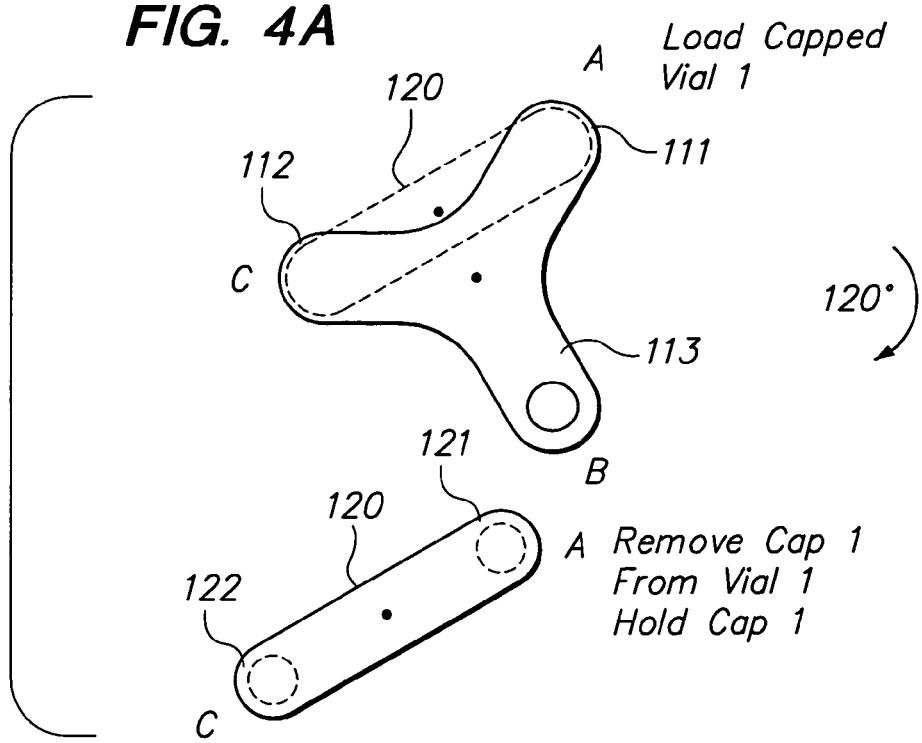

Referring to FIG. 4A, the first member 110 is initially arranged so that lobe 111 is in position A, lobe 112 is in position C, and lobe 113 is in position B. The second member 120 is initially arranged so that lobe 121 is in position A and lobe 122 is in position C. A capped vial (Vial 1) is loaded into a holding member 114 of lobe 111. A spinner mechanism 124 of lobe 121 of the second member 120 removes a cap (Cap 1) from Vial 1. Thus, lobe 111 holds uncapped Vial 1 in position A, and lobe 121 holds Cap 1 for Vial 1 in position A.

Figure 4B:
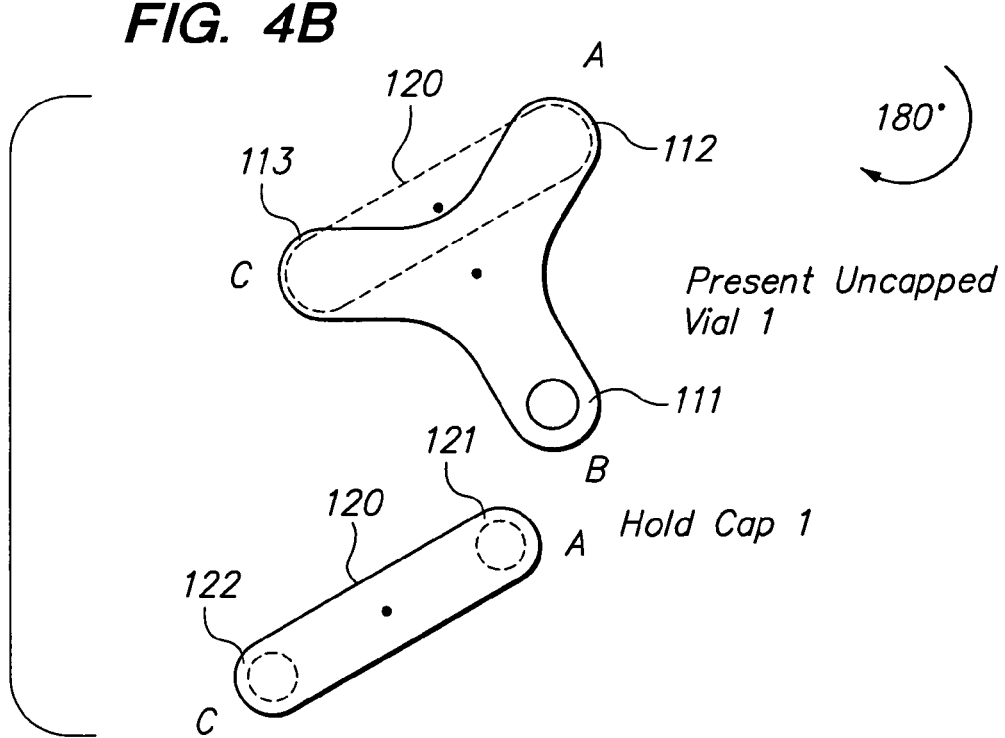

Referring to FIG. 4B, the first member 110 rotates 120 degrees clockwise so that lobe 111 holding the uncapped Vial 1 is moved from position A to position B or to the presentation position. A cytotechnologist can remove Vial 1 from lobe 111, obtain a specimen sample, and return uncapped Vial 1 to lobe 111. Thus, lobe 111 holds uncapped Vial 1 in position B, and lobe 121 still holds Cap 1 for Vial 1 in position A.

Figure 4C:
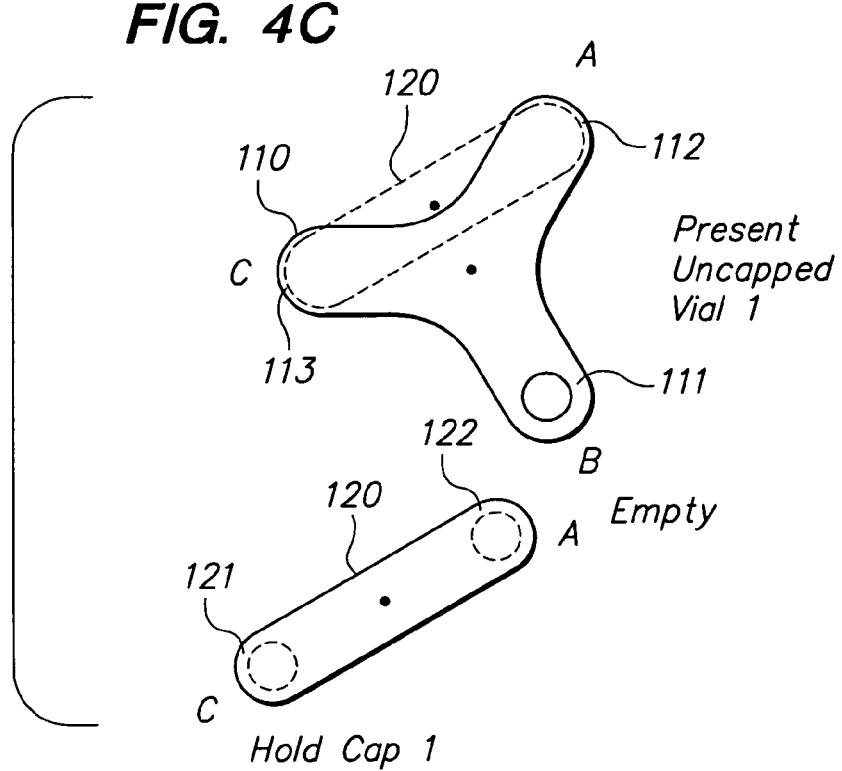

Referring to FIG. 4C, after Cap 1 is removed from Vial 1, or at any time while the uncapped Vial 1 is presented to a cytotechnologist, the second member 120 rotates 180 degrees so that lobe 121 moved from position A to position C, and lobe 122 is moved from position C to position A. Thus, Cap 1 is held by lobe 121 in position C, lobe 122 of the second member 120 is empty, and Vial 1 is held by lobe 111 of the first member 110 in position B.

Figure 4D:
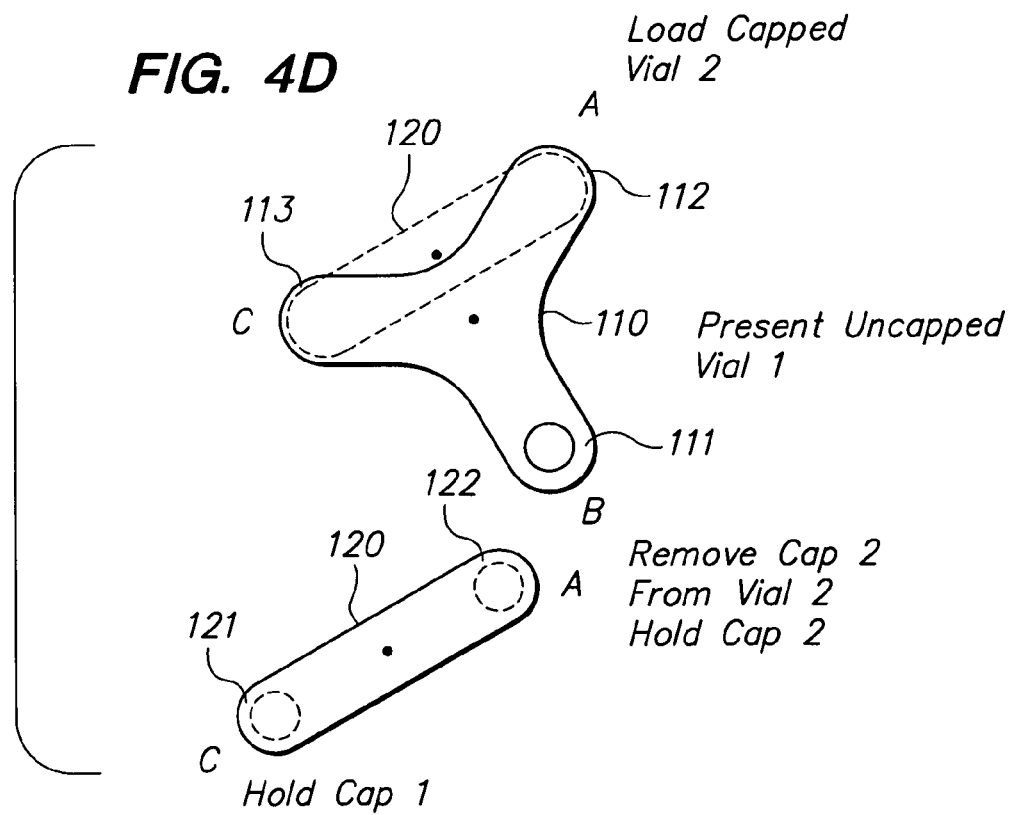

Referring to FIG. 4D, a second capped vial, Vial 2, is loaded from a cartridge or other source into a holding member 114 of lobe 112. A spinner mechanism 124 of lobe 122 of the second member 120 removes a cap (Cap 2) from Vial 2. Thus, lobe 111 of the first member 110 holds uncapped Vial 1 in position B, lobe 112 of the first member 110 holds uncapped Vial 2 in position A, lobe 121 of the second member 120 holds Cap 1 for Vial 1 in position C, and lobe 122 of the second member 120 holds Cap 2 for Vial 2 in position A.

Referring to FIG. 4E, after the cytotechnologist is completed with Vial 1, the first member 110 rotates 120 degrees so that lobe 111 holding open Vial 1 is moved from position B to position C, and lobe 112 holding Vial 2 is moved from position A to position B. The second member 120 is stationary so that lobe 121 holding Cap 1 is also in position C. Vial 1 is also in position C. Lobe 122 holding Cap 2 remains at position A. In position C, Cap 1 is re-applied to Vial 1 by lobe 121 of the second member 120. A cytotechnologist can remove Vial 2 from the holder 114 of lobe 112, obtain a specimen sample, and return uncapped Vial 2 to lobe 112. Additionally, another vial, Vial 3, can be loaded from a cartridge or another source into lobe 113, which is in position A. Thus, lobe 111 holds capped Vial 1, lobe 112 holds uncapped Vial 2, lobe 113 holds recently loaded and capped Vial 3. Lobe 121 of the second member 120 is empty since it used to hold Cap 1, which has now been applied to Vial 1. Lobe 122 holds Cap 2.

Referring to FIG. 4F, the second member 120 is rotated 180 degrees so that empty lobe 121 is moved from position C to position A, and lobe 122, holding Cap 2 for Vial 2 is moved from position A to position C. Thus, both lobe 121 and lobe 113 holding Vial 3 are in position A. A spinner mechanism 124 in lobe 121 removes Cap 3 from Vial 3. Vial 1 is unloaded from lobe 111 into a cartridge or other storage member. Thus, lobe 111 is empty, lobe 112 holds uncapped Vial 2, and lobe 113 holds uncapped Vial 3. Lobe 122, of the second member 120 holds Cap 2, and lobe 121 holds Cap 3.

Figure 4G:
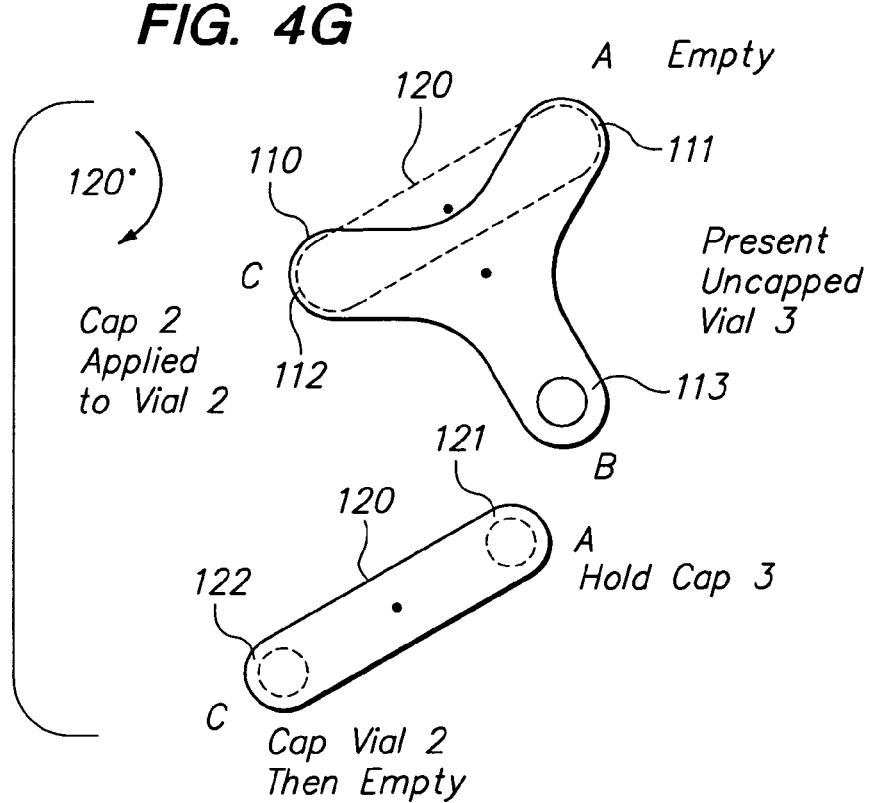

Referring to FIG. 4G, the first member 110 rotates 120 degrees so that lobe 112 holding Vial 2 is moved to position C, lobe 113 holding Vial 3 is moved to position B, and empty lobe 11 is moved to position A. Thus, both lobe 112 holding Vial 2 and lobe 122 holding Cap 2 are in position C. A spinner mechanism 124 in lobe 122 applies Cap 2 to Vial 2, and capped Vial 2 can be unloaded into a cartridge or other storage member.

Figure 4H:
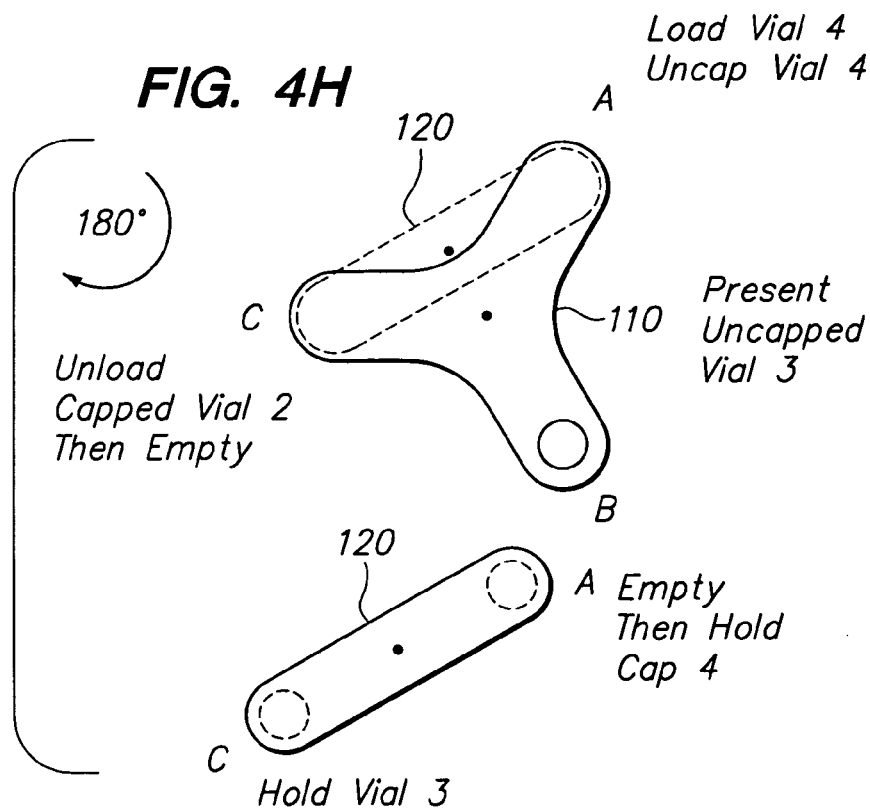
Figure 5:
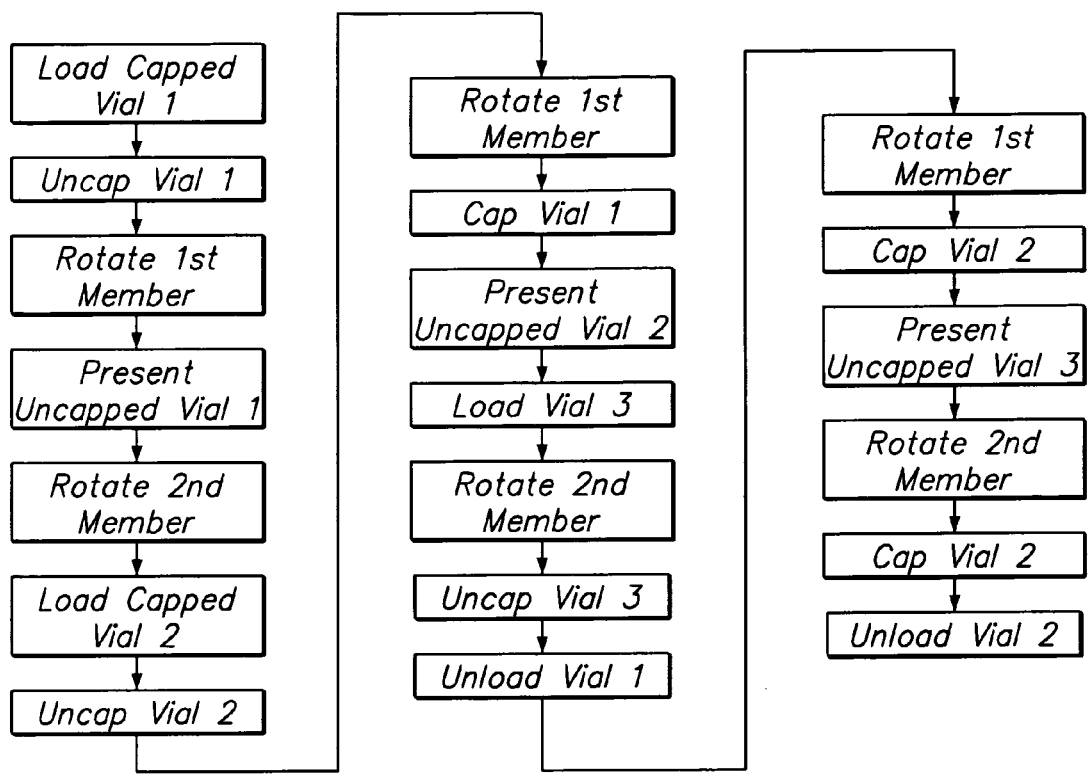
FIG. 5 is a flowchart showing steps of automated vial capping and uncapping according to one embodiment.

Similar processing steps can be repeated as necessary. The beginning of a repetitive cycle is shown in FIG. 4H with the loading and uncapping of a fourth vial, thus providing continuous and automated uncapping, presentation and capping of vials. Continuous and automated capping and uncapping functions are achieved while maintaining the same cap with a particular vial to prevent cross-contamination that can result from placing the wrong cap on a particular vial. Efficient uncapping and capping of vials can be implemented by coordinating the rotation of the first and second members so that loading/uncapping and capping/unloading occur when the first and second members 120 meet at common positions, position A (loading/uncapping) and position C (capping/unloading).

Figure 6A:
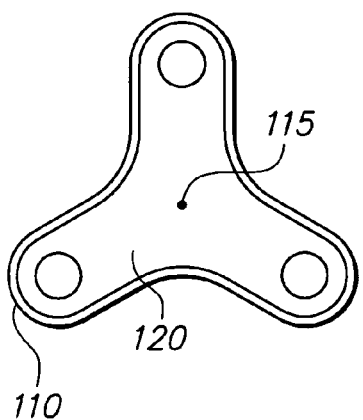
FIGS. 6A-B show an alternative embodiment having a three-lobe vial holding member and a three-lobe uncapping/capping member.
Figure 6B:
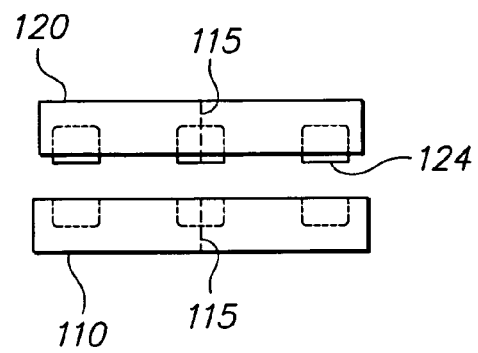

Persons skilled in the art will appreciate that the previously described coordination of two rotatable members can be implemented with first and second members 110 and 120 having different configurations. For example, referring to FIGS. 6A-B, in an alternative embodiment, the second member 120 can have a shape that is similar to the first member 110. In the illustrated embodiment, both the first and second members 110 and 120 have three lobes. Thus, the first and second members 110 and 120 can share a common axis 115, and rotation of the first and second members 110 and 120 can be coordinated in a similar manner previously described to achieve automated, continuous uncapping and capping of vials.

Vials can also be loaded and unloaded in various manners. For example, vials can be manually loaded by a cytotechnologist. Further, vials can be presented in a cartridge or other storage element for larger-scale continuous operations.

Figure 7:
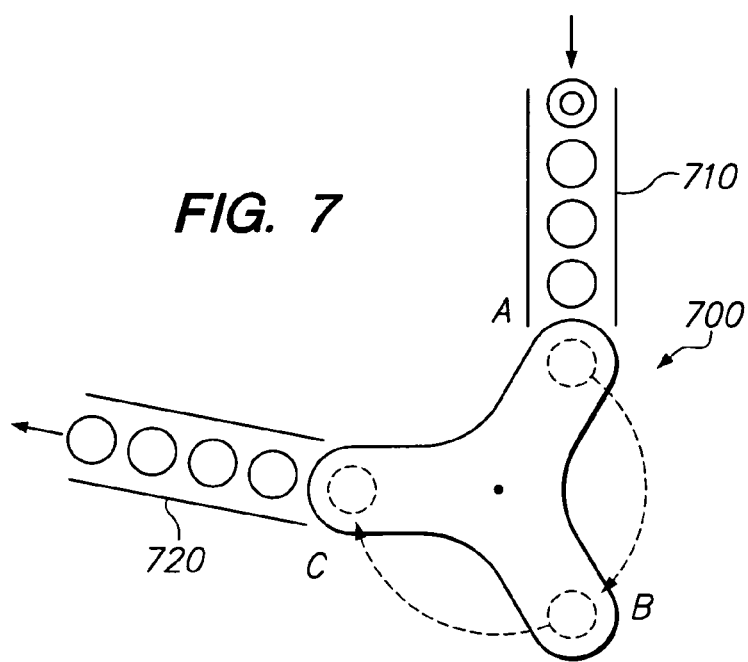
FIG. 7 illustrates cartridges that are used to load and unload vials relative to a three-lobe vial holding member according to one embodiment.

For example, FIG. 7 illustrates an open-ended horizontal loading/unloading system 700 that includes a loading or feed chute or cartridge 710 and an unloading or exit chute or cartridge 720. Capped vials are provided to the feed cartridge 710 and slide along the bottom of the cartridge 710 to position A (loading/uncapping) of the first member 110 in a passive manner, e.g., by the force of other vials, or with an active element, such as a conveyor, a belt or other transport device. The vials that are loaded into the first member 110 are processed in a similar manner as previously described. After the cytotechnologist is completed with the vial and the vial is re-capped, vials exiting the first member 110 at position C are pushed along the bottom of the exit cartridge 720 for further processing or to a cartridge for storage. A bottom surface of the exit cartridge 720 can include a coating, such as a Teflon® to facilitate vials being pushed along the bottom surface of the cartridge 720.

Figure 8:
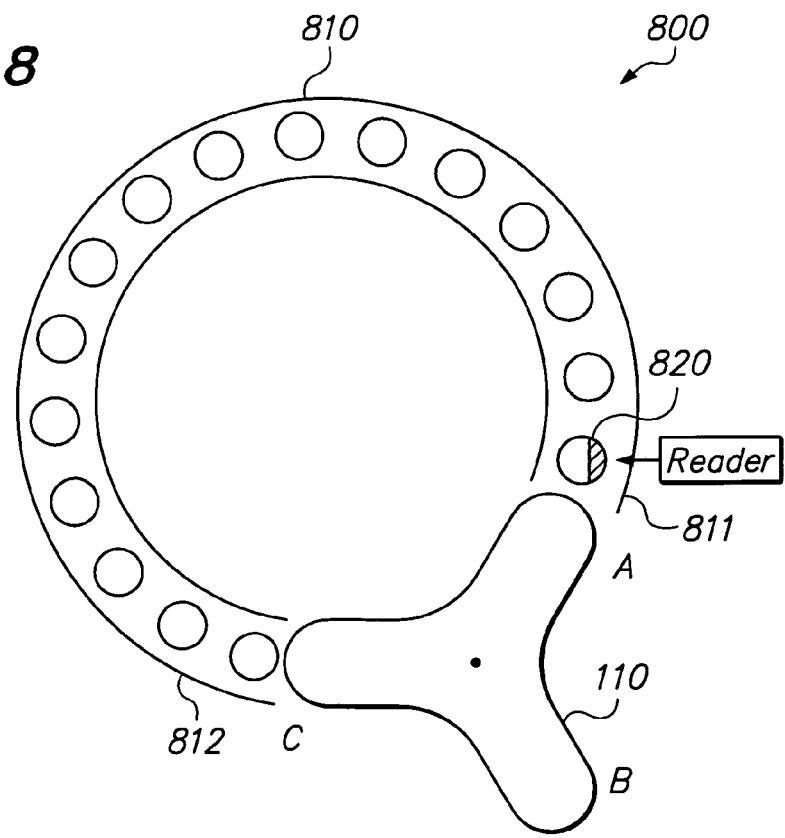
FIG. 8 illustrates a circular or continuous cartridge that is used to load and unload vials relative to a three-lobe vial holding member according to another embodiment.

FIG. 8 illustrates an alternative embodiment of a closed loading/unloading system 800. In this embodiment, one end 811 of a cartridge 810 is connected to an input to the first member 110 and position A (loading/uncapping). The other end 812 of the cartridge 810 is connected to an output of the first member 110 at the capping/unloading position C. A batch of vials can be processed as previously described.

To ensure that processing and sampling of vials is not repeated, one of the vials can be marked as the "first" vial. For example, a particular marking or code 820, such as a barcode, can identify a particular vial as the first vial in the cartridge 810. A reader 830, such as a bar-code reader or other suitable device, can scan the codes of the vials as they are loaded into the first member 110. When all of the vials are processed and the first vial is ready to be loaded again into the first member, the reader 830 can provide an indication or control signal that all of the vials have been processed, and a new batch of vials or new cartridge 810 can be loaded. An example of a mechanical method would be a door, flap, pin, etc. that tracks between the last new & the first old vials. When it's at the uncapping position, the used vial cannot physically be loaded.

Figure 9:
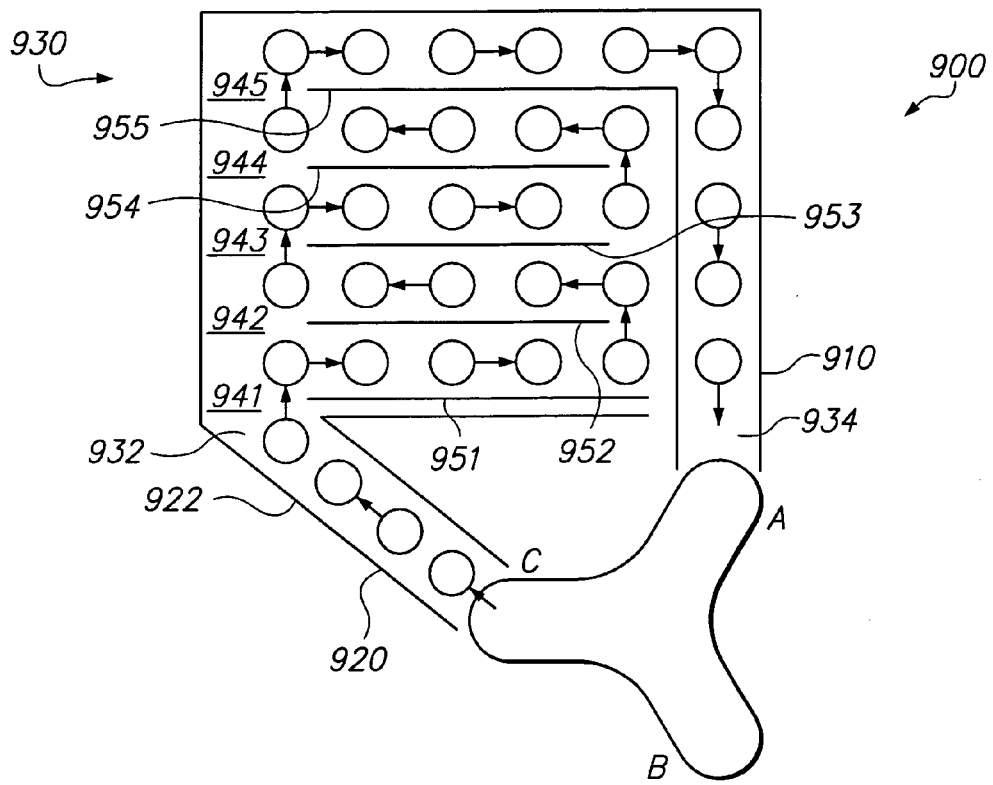
FIG. 9 illustrates a vial storage element and cartridges that are used to load and unload vials relative to a three-lobe vial holding member according to a further embodiment.

FIG. 9 illustrates a top view of a further alternative embodiment of a loading and unloading system 900. This system 900 includes a loading or feed cartridge 910, an unloading or exit cartridge 920, and a vial storage element 930. In the illustrated embodiment, the vial storage element 930 is a horizontal storage element in which vials move and slide horizontally along a bottom surface of the vial storage element 930. The storage element 930 has an inlet 932 and an outlet 934. An outlet 934 may be connected to an inlet 911 of the loading cartridge 910, and the inlet 932 may be connected to an outlet 921 of the unloading cartridge 920.

In the illustrated embodiment, the storage element 930 is configured so that vials slide along the bottom of the storage element and travel back and forth within the storage element. A storage element can include various numbers of rows. The illustrated embodiment includes five rows 941-945 of vials. The vials can rest on storage element support or floor members 951-955. A top row 945 vial is provided to the loading cartridge 910, processed, and unloaded to the exit cartridge 920.

The unloaded vial slides along the bottom surface of the storage element 930 to the bottom row 941, slides left to right along support member 951, slides up to the next row 942, slides right to left along support member 952, slides up to the next row 943, slides left to right along support member 953, slides up to the next row 947, slides right to left along support member 954, and slides up to the top row 945, and slides left to right along support member 955, until the first vial reaches its beginning point. Indeed, persons skilled in the art will appreciate that a storage element 930 can have various numbers of rows, and that different numbers of vials occupy different sized rows. Accordingly, the particular configuration shown in FIG. 9 is provided for purposes of illustration and explanation, not limitation.

Vials can be passively or actively moved through the different levels of the storage element 930. For example, the vials can be passively moved through the storage element 930 by being pushed by other vials as they exit a lobe of a rotating member. The bottom surfaces of the support members can be coated with a low friction coating such as Teflon® in order to reduce the friction between the bottoms of the vials and the bottom surface of the storage element 930.

Vials can also be moved using a conveyor, belt or other active device. Different vial transport systems may be used depending on, for example, the number, size and weight of vials, the number of levels or rows in the storage element, and the number of vials stored per row. Whether passive can be used may depend on the size of the storage element and the number of vials to be pushed within the storage element.

Further, one of the vials can be marked as the first vial so that a reader can identify the first vial and provide an indication that a new batch of vials should be loaded. Additionally, the horizontal storage elements 71, 72, 810 and 930 shown in FIGS. 7-9 can be stacked. Control mechanisms can be used to transfer vials between levels of storage elements. In a further alternative embodiment, the vial storage element can be a vertical storage element rather than a horizontal storage element as shown in FIGS. 7-9.

The previously described embodiments can also be configured to allow a cytotechnologist to control the system so that a new uncapped vial is not presented in response to a particular user input. For example, if a cytotechnologist leaves the laboratory, it is desirable that an uncapped vial does not remain open when the cytotechnologist is not present to obtain or process the samples. Thus, in order to prevent uncapped vials from being left open out for extended periods of time, a system can be configured so that the first member 110, for example, is disengaged so that an uncapped vial is not delivered to the presentation position B and exposed to potentially contaminated environments for extended periods of time. This could be done using a manual switch, a solenoid or another suitable control device.

Embodiments provide an apparatus and method that improves the handling and processing of vials to prepare specimen slides. A cytotechnologist is not required to manually remove a cap, mark and/or track caps that are associated with particular vials, or manually replace the cap. Rather, the uncapping and capping steps are automated, and it is no longer necessary to mark and track caps and vials since a vial that is associated with a particular cap is automatically placed on that vial when a specimen sample has been obtained. Thus, embodiments provide for more efficient and accurate slide processing and analysis that eliminates tedious, repetitive manuals tasks and provides for more effective slide processing and analysis of specimen samples. Further, automated uncapping and capping are performed while eliminating or greatly reducing contamination of specimen samples.

Another embodiment provides a slide cartridge that holds slides horizontally on one side or at least partially on one side. The cartridge includes a bottom recess. Slides are dispensed from the cartridge through the bottom recess.

Figure 10A:
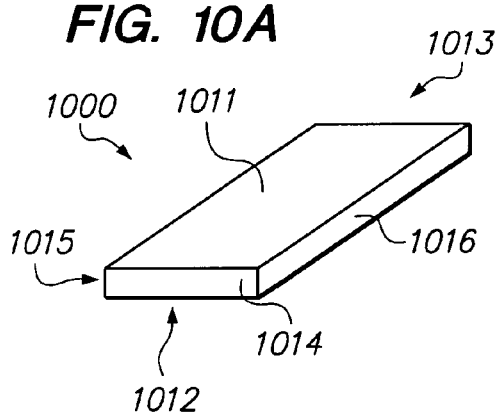
FIG. 10A illustrates a typical specimen slide.
Figure 10B:
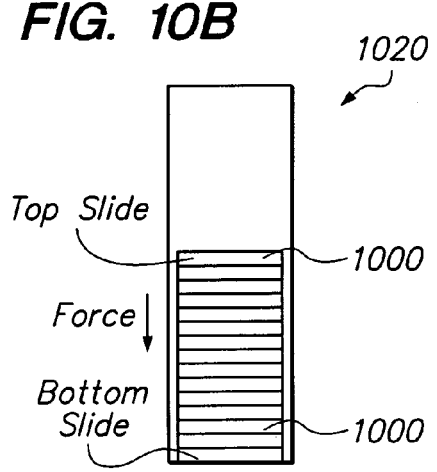
FIG. 10B illustrates a known slide cartridge that includes vertically stacked slides, one on top of another.

Referring to FIG. 10A, a typical specimen slide 1000 includes a top surface 1011, a bottom surface 1012, two edges 1013 and 1014 and two sides 1015 and 1016. Referring to FIG. 10B, a known slide cartridge 1020 holds a plurality of slides 1000. More particularly, the slides 1000 are stacked in a "top-bottom" arrangement or "top surface 1011 to bottom surface 1012" arrangement. In other words, the slides are stacked one on top of another. As a result, the bottom slide in the stack is subjected to the weight of each of the other slides above the bottom slide. This arrangement and the force exerted on the bottom slide being removed from the stack can present problems when picking the bottom slide, e.g., picking multiple slides and irregular movements, such as tidly-winking, as discussed earlier in the Background.

Figure 11A:
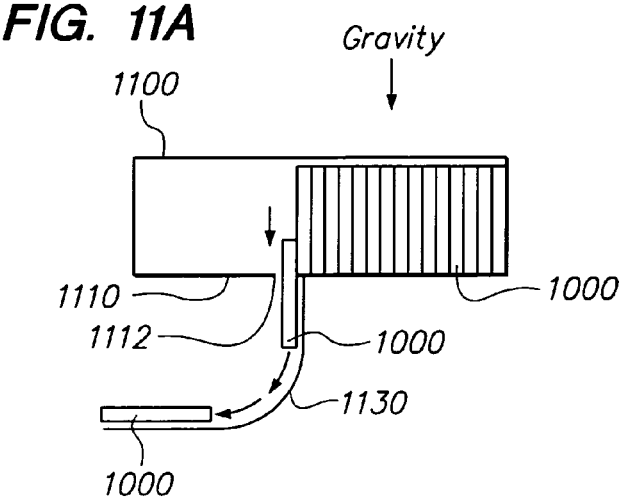
FIGS. 11A-B illustrate a slide cartridge or slide dispensing module according to one embodiment in which slides are horizontally stacked on and dispensed through a bottom recess formed in the cartridge and along a ramp.
Figure 11B:
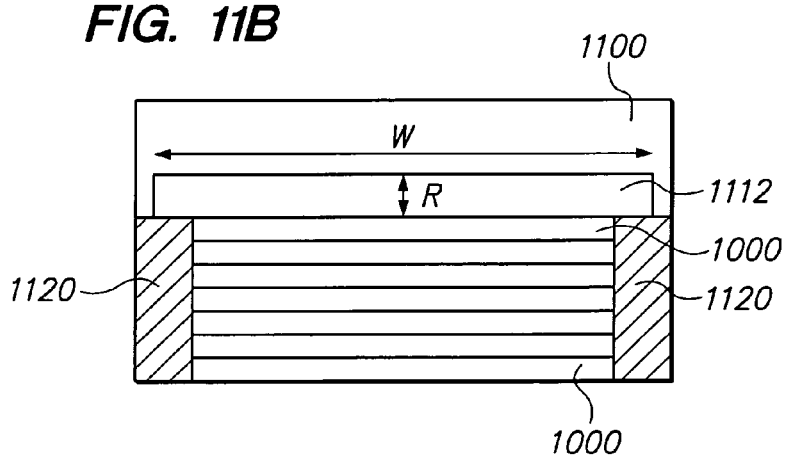
Figure 12A:
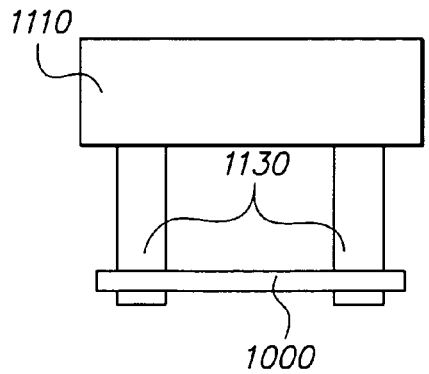
FIGS. 12A-B are partial front and top views of a slide that is dispensed from a cartridge and on a ramp.
Figure 12B:
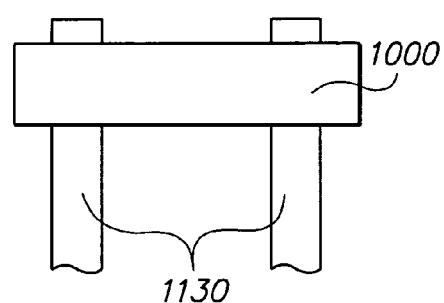
Figure 13:
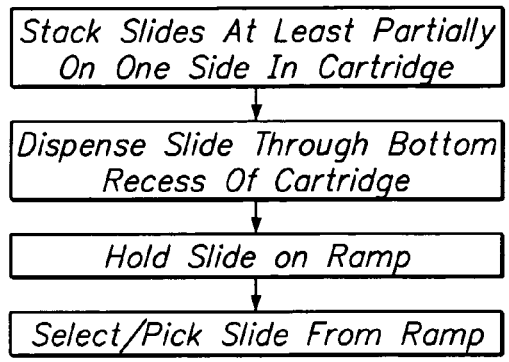
FIG. 13 is a flow diagram showing how slides are arranged in and dispensed from a cartridge according to one embodiment.

Referring to FIGS. 11A-B, according to one embodiment, a slide cartridge 1100 holds a plurality of slides 1000 horizontally or at least partially on one side, as opposed to stacking slides on top of each other in a "top-bottom" arrangement as in known slide cartridges.

Slides can be stacked in the cartridge 1100 so that they stand up on one side or partially on one side. In the illustrated embodiment, the sides 1015 and 1016 (generally 1015) are longer than the edges 1013 and 1014 (generally 1013). Slides are on their sides 1015 so that each slide stands up on a side 1015 inside the cartridge 1100. Embodiments, however are not so limited. For example, some slides may have shapes that are more similar to a square than a rectangle. Such slides can be stacked at least partially on a side 1015 or at least partially on an edge 1013 since an edge may be the same as or similar to a side. For purposes of explanation, not limitation, this specification refers to and illustrates rectangle-shaped slides having sides 1015 that are longer than their edges 1012 and slides being stacked within a cartridge 1100 so that they stand up on one side or partially on one side. Persons skilled in the art will appreciate that other slide configurations can also be utilized so that slides are stacked at least partially on a side or at least partially on an edge.

Continuing with reference to FIG. 11A, the cartridge 1100 has a bottom surface or floor 1110 having an aperture or opening 1112. The width "w" and length "l" of the aperture 1112 are larger than the width and length or height of a side 1015 of the slide (otherwise referred to as the thickness of the slide). The width "w" and the length "l" are sized so that one slide passes through the aperture 1112 at a time. For example, a thickness of a typical slide can range from about 0.035" to about 0.041", and a length of a side of slide is about 3", e.g., about 2.985" to about 2.991". For these exemplary rectangle-shaped slides, the width "w" of the aperture 1112 can be about 0.05", e.g., about 0.051" to about 0.059", and the length "l" of the aperture 1112 can be about 3", e.g., about 3.02 to about 3.04". An aperture 1112 having these dimensions has been determined to allow one slide to pass through the aperture 1112 at a time. Indeed, other aperture 1112 dimensions can be used with different slide configurations and dimensions.

FIG. 11B illustrates a cartridge 1100 having optional edge buffer or support members 1120. The buffer or support members can provide further support to the edges 1013 of the slides as they are pushed through the cartridge 1100, and are dispensed through the aperture 1112 formed in the bottom 1110 of the cartridge 1100.

In the embodiment shown in FIGS. 11A-B, 12A-B and 13, a slide that is stacked on its side is dispensed from the bottom 1110 of the cartridge 1100 through the aperture 1112 and onto a holding member 1130, such as a ramp or a slide (generally ramp 1130). Thus, the primary vertical force that is applied to each slide inside the cartridge 1100 is gravity, as opposed to conventional cartridges 1000 (FIG. 10) that stack slides one on top of the other.

In the illustrated embodiment, the ramp 1130 includes arcuate ramp members. A slide 1000 exits the cartridge 1100 and drops onto a top vertical section of the ramp members 1130. The dispensed slide slides along the ramp members 1130 until the slide comes to rest on a flat or bottom portion of the ramp members 1130 where it can be selected or picked by a slide platform or other equipment. In the illustrated embodiment, the top and bottom sections of the ramp 1130 are generally perpendicular to each other. Thus, the slide is rotated about 90 degrees between being dispensed from the cartridge 1100 and coming to rest on the ramp 1130.

The ramp 1130 can have various shapes and sizes depending on, for example, the orientation of the slides inside the cartridge 1100 and design of the equipment that is used to pick the slide from the ramp 1130. For example, as shown in FIGS. 11A-B and 12A-B, the illustrated ramp 1130 is arcuate and generally forms an angle of about a 90 degrees. Other ramp designs that can be used include elliptical-shaped ramps or other ramp designs that appropriately position a slide on the ramp and beneath the cartridge 1100.

Figure 14A:
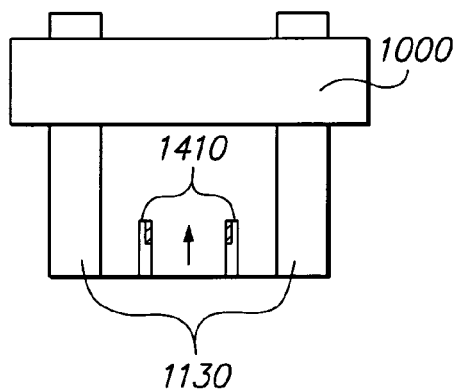
FIGS. 14A-C are partial top views of stages of a slide that is dispensed from a cartridge and being selected or picked by slide handling or processing equipment.

In one application, referring to FIGS. 14A and, 15A, a slide platform 1400 having slide support members or fingers 1410 approaches the ramp 1130. An approaching slide platform 1400 may trigger the cartridge 1100 to dispense a slide 1000, or a slide 1000 may be waiting for the platform 1400, as shown in FIG. 14A. The fingers 1410, which may be extended from the platform 1400, are spaced apart from each other to support a slide 1000 thereon. The fingers 1410 are also spaced sufficiently close to each other so that they can pass between the ramp members 1130.

Figure 14B:
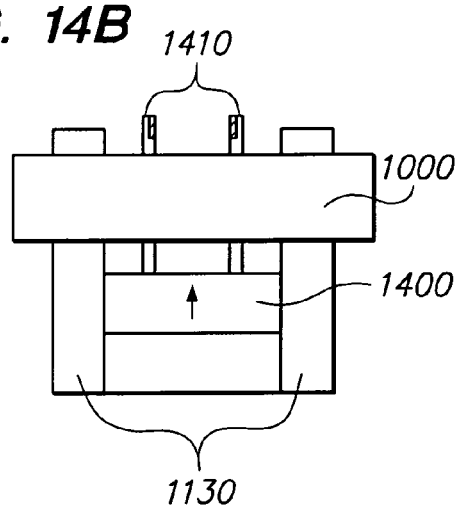
Figure 14C:
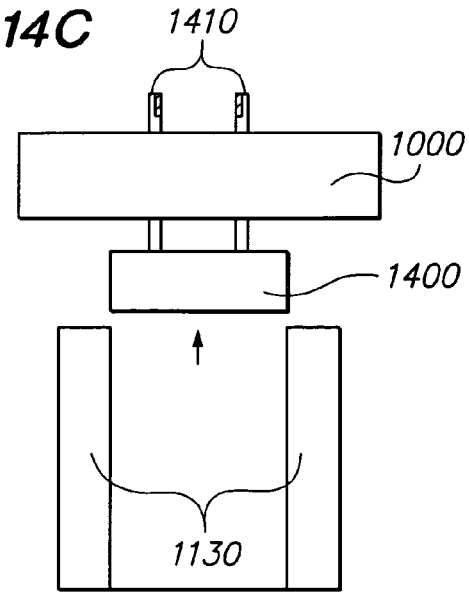
Figure 15A:
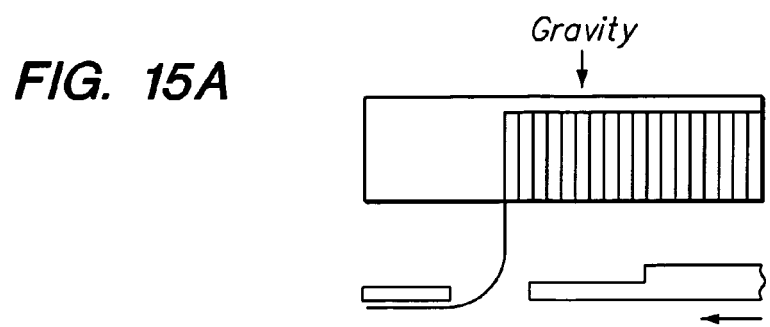
FIGS. 15A-C are side views of stages of a slide that is dispensed from a cartridge and being selected or picked by slide handling or processing equipment.
Figure 15B:
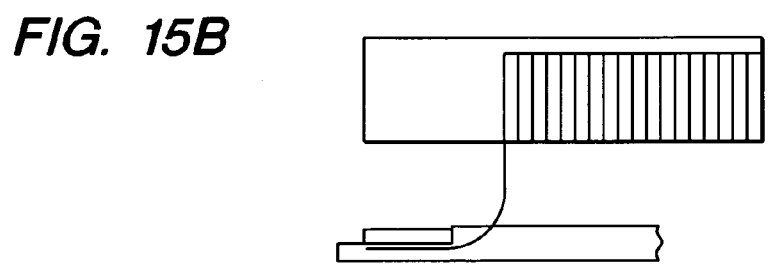
Figure 15C:
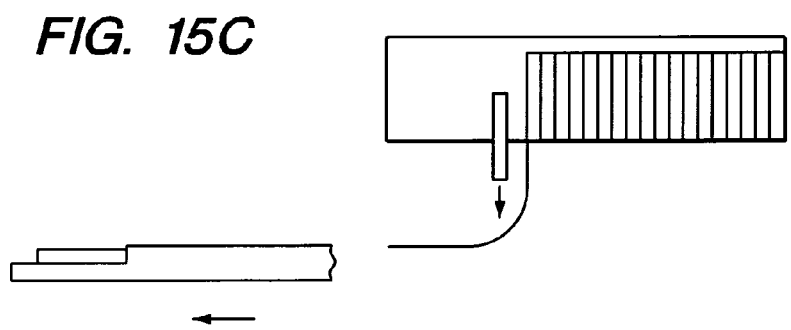

Referring to FIGS. 14B and 15B, the fingers 1410 pick the slide 1000 that is held by the ramp members 1130, and the slide 1000 is placed on the fingers 1410. Referring to FIGS. 14C and 15C, the platform 1400 and the fingers 1410 having the slide 1000 thereon move past the ramp 1130, removing the slide 1000 from the ramp 1130. Another slide 1000 can then be dispensed from the cartridge 1100 and placed on the ramp 1130 for the next platform 1400 or for the next pass of the same platform 1400 after the selected slide is unloaded.

Figure 16:
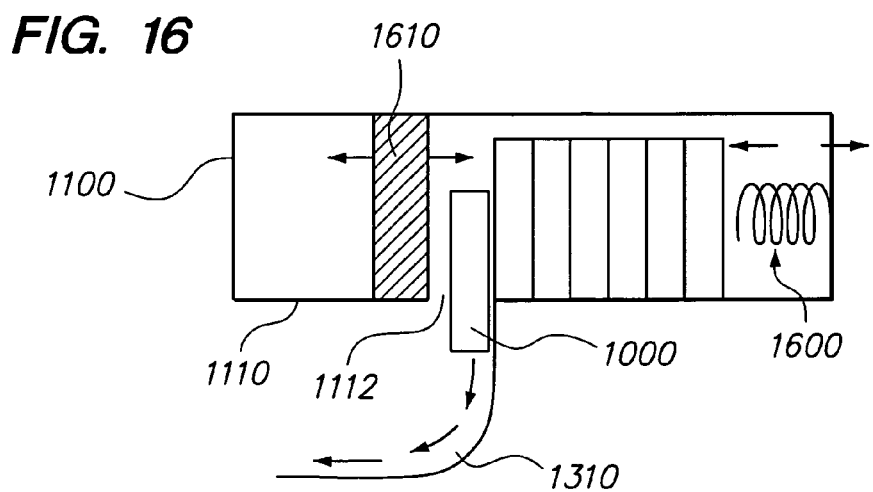
FIG. 16 illustrates an embodiment of a slide dispensing module that moves slides within the module using a spring.

Various mechanisms can be used to draw out or dispense a slide from the cartridge 1100 and dispense the slide through the bottom recess 1112 and onto the ramp 1130. For example, as shown in FIG. 16, the cartridge 1100 can include spring 1600. The spring 1600 pushes slides 1000 against a stop 1610. The spring 1600 can be actuated to push the next slide over towards the stop 1610 to be dispensed through the aperture 1112 formed in the bottom of the cartridge 1100. The spring 1610 can be passive, or actuated with, for example, a solenoid or other mechanical or electromechanical device. For example, as a slide selection platform 1400 approaches the ramp 1310, the platform 1400 may activate or engage the spring 1600, thereby pushing the spring 1600 against a slide 1000, and forcing the next slide 1000 to be dispensed from the cartridge 1100 and onto the ramp 1130, where it can be picked off of the ramp 1130 by fingers 1410 of the platform 1400 moving underneath the cartridge 1100 and past the ramp members 1130. Alternatively, the stop 1610 can be moved between covering the recess 1112 and opening the recess 1112, thus selectively allowing a slide to pass through the recess 1112.

Figure 17A:
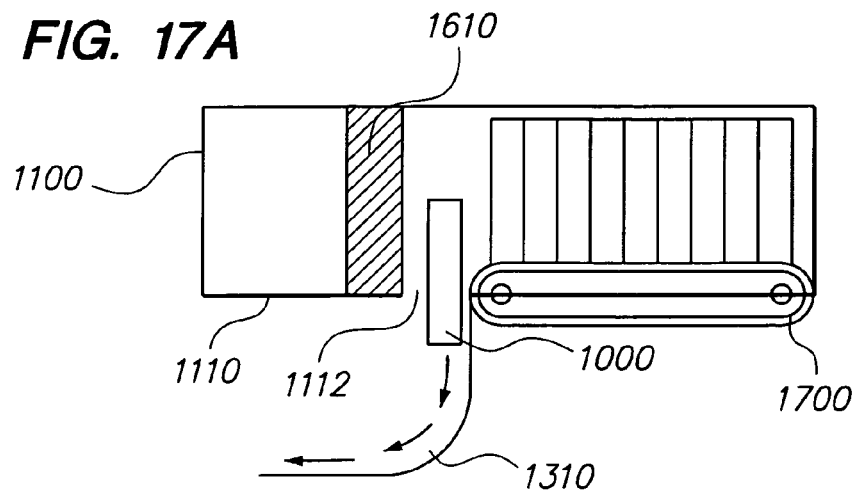
FIG. 17A illustrates an embodiment of a slide dispensing module that moves slides within the module using a conveyor or transport member.

FIG. 17A illustrates another mechanism that can be used to dispense slides 1000 from the cartridge 1110 through the bottom recess 1112. In this embodiment, slides 1000 rest on a conveyor element or belt 1700. The conveyor 1700 can be inside the cartridge 1100, or partially inside and partially outside of the cartridge 1100. The conveyor 1700 can be moved so that the next slide at the end of the conveyor 1700 drops down through the aperture 1112 and onto the ramp 1130. Actuation of the conveyor 1700 can be coordinated with an approaching slide platform 1400 that picks the slide 1000 from the ramp 1130.

In another embodiment, shown in FIGS. 17B-F, the holding member below the cartridge is a belt mechanism 1720 in the form of a ramp and support members 1730, which assist the slide in its decent down to the end of the ramp where it can be selected by fingers 1410. The belt 1720, like the holding member shown in FIGS. 14A-C, can include two spaced belt members (generally "belt") that allow fingers 1410 to pass between and select a slide from the belt 1720.

In the illustrated embodiment, the belt 1720 rotates around hinges 1722 and is restrained to have an "L" type or angled shape. Attached to the outer surfaces of the belt 1720 are support members 1730. In the illustrated embodiment, the support members 1730 are also "L" shaped and form a groove or angle 1732 for receiving an end of a slide. The belt 1720 and support member 1730 may have different designs depending on the cartridge and system configurations. As the belt 1720 rotates, the support members 1730 also rotate along the outer surface of the belt and around the hinges 1722.

Figure 17B:
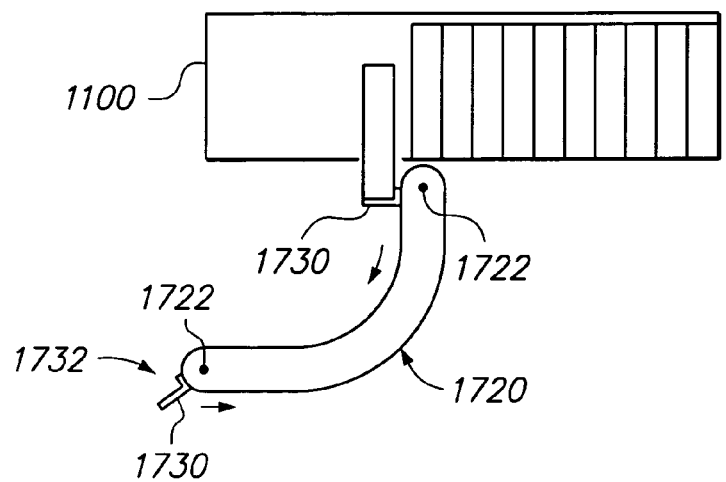
FIGS. 17B-F illustrate an embodiment of a slide dispensing module that has a ramp in the form of a belt that moves slides down the belt with the assistance of a support member or foot on the belt.
Figure 17C:
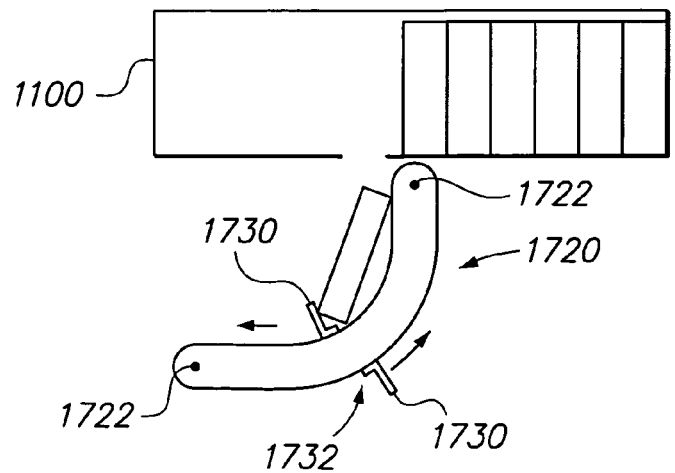

In use, referring to FIG. 17B, the belt 1720 is rotated to a cartridge position or start position so that the support member 1730 that is adjacent to the cartridge 1100 receives a slide that is dispensed through a recess formed in the bottom of the cartridge 1100. The other support member 1730 is empty and at the end of the belt 1720 or at the unloading position. The slide falls down onto the support member and into the receiving groove. The belt 1720 is rotated, thereby moving the support member 1730 and the slide supported thereby downward, as shown in FIG. 17C. At the same time, the empty support member 1730 that was initially at the unloading position moves upward along the backside of the belt 1720.

With this embodiment, one end of the slide is held above the belt 1720 by the support member 1730, and the other end of the slide rests on the belt 1720 and is assisted in its descent by gravity. As a result, the amount of friction between the slide and the belt holding member is reduced since one end and a substantial portion of the bottom of the slide are not initially in contact with the belt 1720.

Figure 17D:
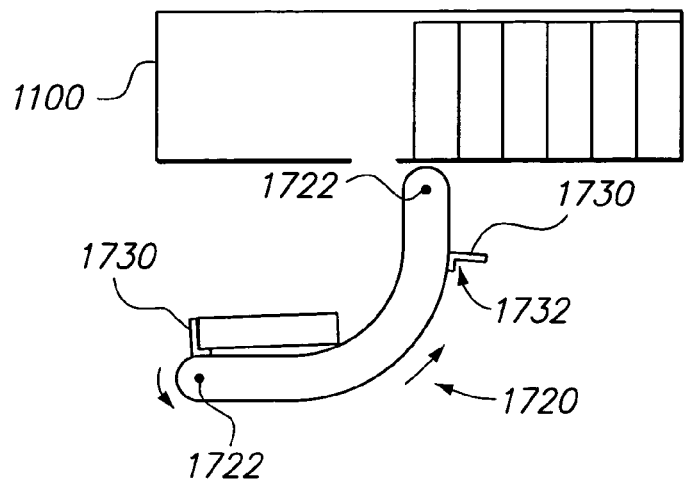
Figure 17E:
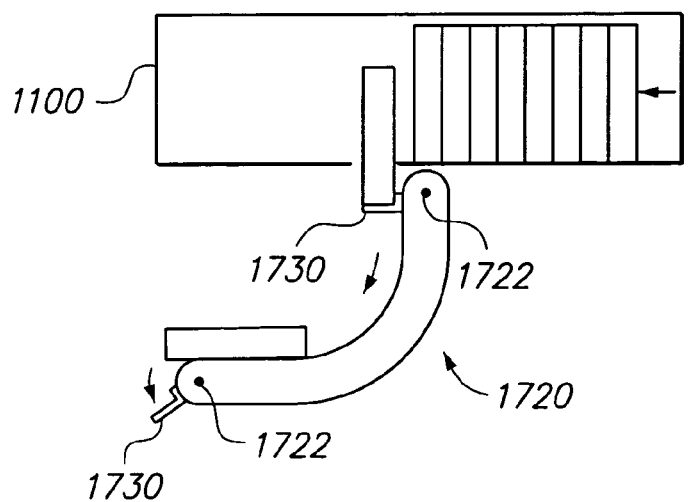
Figure 17F:
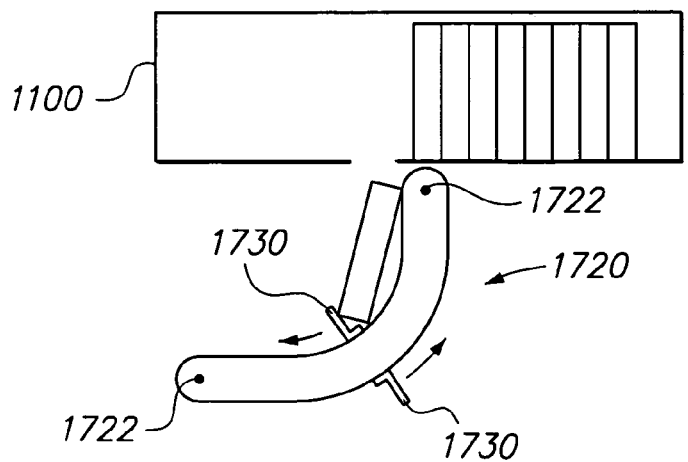

As the belt 1720 rotates further, referring to FIG. 17D, the support member 1730 and the slide are positioned at the end of the belt 1720 or at the unloading position. At the same time, the empty support member 1730 proceeds further up the backside of the belt 1720 towards the cartridge 1100. Referring to FIG. 17E, the belt 1720 is rotated further and, as a result, the support member 1730 that was carrying the slide rotates around the front end of the belt 1720 and around a hinge 1722, thereby dropping the slide onto the end of the belt 1720 at the unloading position. The slide can then be picked by fingers 1410 that carry the slide to a processing or other station.

The support member 1730 that has traveled around the top of the belt 1720 and around the top hinge 1722 is now ready to receive the next slide from the cartridge 1100, and the next slide drops down onto the support member 1730 that was previously empty. The next slide is then supported by the support member 1730 as it descends down the belt 1720, and this process can be repeated to dispense other slides from the cartridge 1100.

Figure 18:
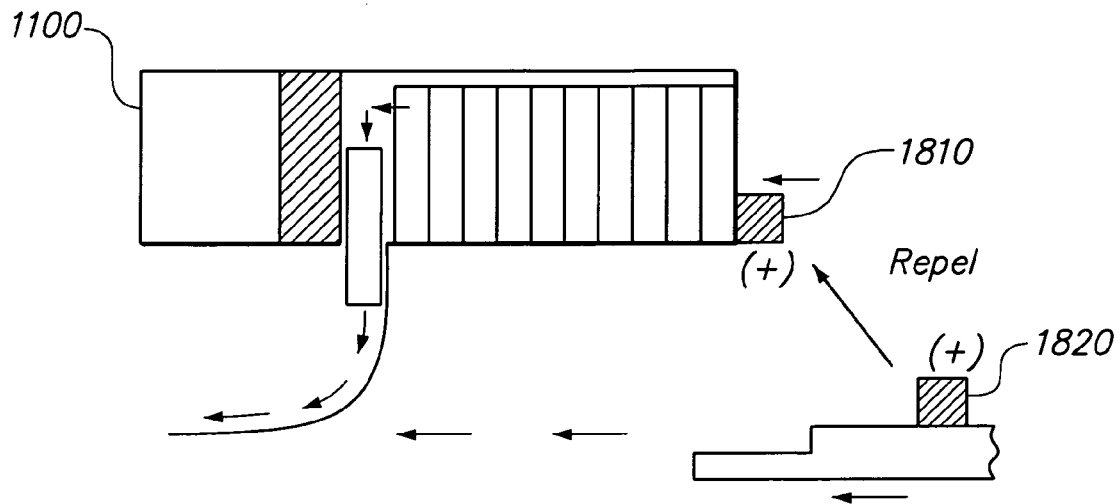
FIG. 18 shows a slide cartridge that moves slides towards a button recess in the cartridge using repulsive magnetic forces.

In a further embodiment, referring to FIG. 18, slides can be displaced towards the aperture 1112 using magnetic forces. For example, one end of the cartridge 1100 can have a first magnetic element 1810, and a slide platform 1400 can have a second magnetic element 1820. Movement of the first magnetic element 1810 can cause movement of the slides 1000 inside the cartridge 1100.

The first and second magnetic elements 1810 and 1820 can be similarly charged so that they repel each other. Thus, as the slide platform 1400 and second magnetic element attached thereto approach the cartridge 1100 and the first magnetic element 1810, the magnets 1810 and 1820 repel each other, causing a slide 1000 to be displaced towards the aperture 1112. As a result of movement, and the next slide 1000 is dispensed through the aperture 1112 and onto the ramp 1130. Fingers 1410 of the slide platform 1400 pick the slide 1000 from the ramp 1130 and deliver the slide 1000 to a processing station or other destination as needed. Persons skilled in the art will appreciate that various magnitudes of repulsive magnetic forces can be used depending on, for example, the number of slides in the cartridge, the distance between magnetic elements and the speed at which the slide platform approaches the cartridge. Further, the platform and cartridge can be configured to displace slides using attractive magnetic forces, e.g., a magnet element can attract or pull a magnet 1810 on the cartridge 1100, thus pulling the cartridge magnet 1810 and causing a slide to exit the cartridge through the recess 1112.

Figure 19A:
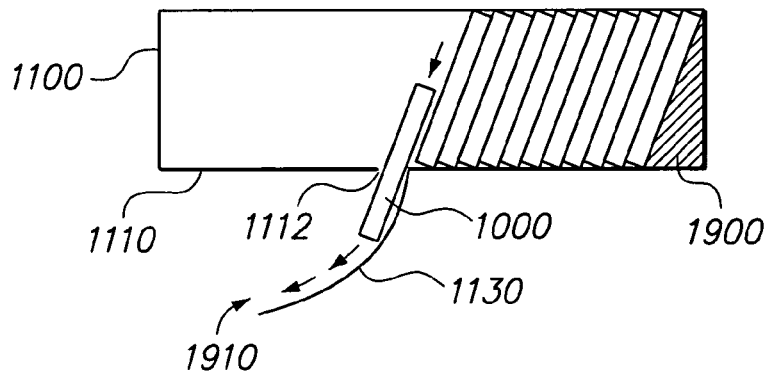
FIGS. 19A-B show a slide cartridge according to another embodiment in which slides are partially stacked on edge or at an angle and dispensed through a bottom recess in the cartridge along a ramp.
Figure 19B:
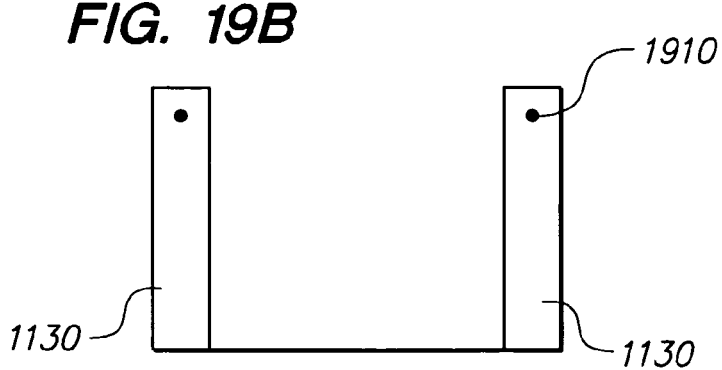

In further embodiments, a combination of the configurations shown in FIGS. 16-18 can be used. For example, a cartridge that moves slides within the module may include both a spring (as in FIG. 16) and a conveyor or transport member (FIG. 17). In a further embodiment, a cartridge may include a spring (FIG. 16) and repulsive magnetic forces (FIG. 18). In a further embodiment, a cartridge may include a conveyor or transport member (FIG. 17A) and magnets (FIG. 18). Various combinations may also include the belt 1720 and support members 1730 (FIGS. 17B-F). Indeed, various configurations can be utilized to move slides within a cartridge depending on the design of a particular system. FIGS. 19A-B illustrate a further alternative embodiment in which the slides are stacked partially on one side 1115 in the cartridge 1100. In this embodiment, the cartridge 1100 includes an angled stop 1900. Slides 1000 are positioned at an angle or partially on one side against the angled stop 1900. For example, the slides 1000 may be arranged in the cartridge 1100 at an angle, for example, from about 45-90 degrees, e.g., about 60-75 degrees with respect to a horizontal or a bottom surface 1110 of the cartridge 1100. Persons skilled in the art will appreciate that other angular arrangements can also be utilized, and that 45-90 degrees is provided as one exemplary range of angles for purposes of explanation and illustration, not limitation. The aperture 1112 is sized so that one slide 1000 passes at an angle through the aperture 1112 at a time. Thus, the size of the aperture 1112 may be slightly larger than the aperture 1112 that is used when slides are in to accommodate one slide 1000 passing through the aperture 1112 at an angle stacked on one side.

For example, the slides 1000 can be arranged at an angle of about 60-75 degrees inside the cartridge 1100 and dispensed from the cartridge 1100 through the aperture 1112 at an angle of about 10-45 degrees. The slides 1000 can be disposed from the cartridge 1100 onto a ramp 1130, as previously described.

In this embodiment, the ramp 1130 can have members that are more elliptically shaped and may be shorter than the ramp described with respect to FIGS. 11A-14C. Further, the ramp 1130 can have a softer descent than the ramp shown in FIGS. 11A-14C having sections that are generally perpendicular to each other. Thus, the end of the ramp 1130 may be at an angle rather than being flat or horizontal. For example a slide 1000 held by the ramp 1130 may be held at an angle of about 10-45 degrees.

The ramp 1130 can have a stop 1910 to ensure that the slide does not fall off the ramp 1130 when the slide 1000 is held on the ramp 1130 at an angle. For example, in the illustrated embodiment, an end of the ramp 1130 includes a stop bump 1910. Thus, as the slide 1000 is dispensed from the cartridge 1100 and slides along the ramp members 1130 until one end of the slide contacts the stop bump 1910. As a result, the slide 1000 can be maintained on the ramp 1130 at an angle, one end of the slide being lower than the other end of the a slide. The slide may come to rest at an angle of about 10-45 degrees with respect to a horizontal. Positioning the slide in this manner allows fingers 1410 of a slide platform 1400 to engage the end of the slide that is held by the stop bump 1410.

Figure 20A:
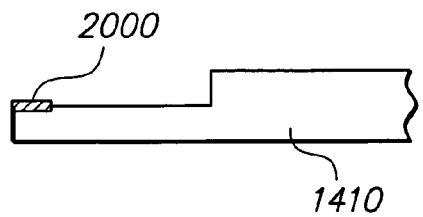
FIGS. 20A-B are side and top views of fingers of a slide selection platform having a friction surface or pad at the end thereof.
Figure 20B:
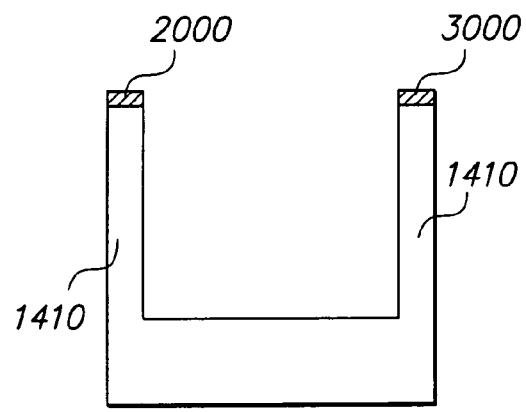
Figure 20C:
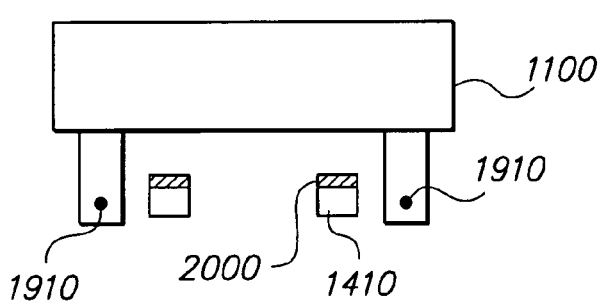
FIG. 20C is a front view illustrating fingers of a slide selection platform relative to a ramp.
Figure 21A:
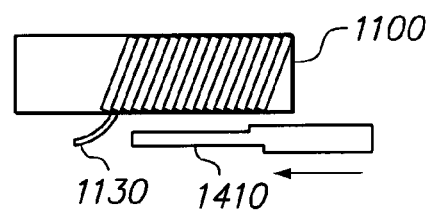
Figure 21B:
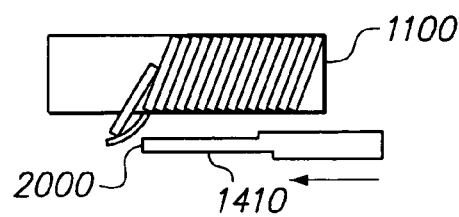
Figure 21C:
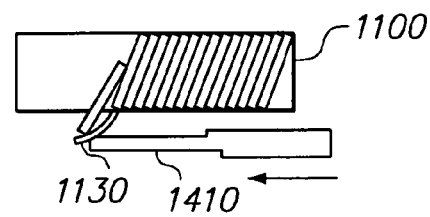
Figure 21D:
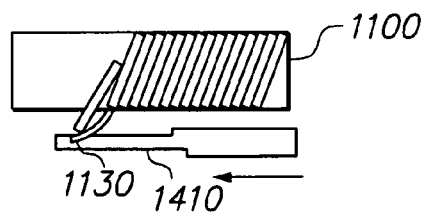
Figure 21E:
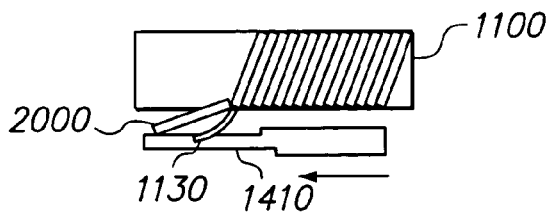

For example, referring to FIGS. 20A-B, ends of fingers 1410 of a slide selection platform 1400 can include a friction surface or pad 2000. In use, referring to FIGS. 21A-G, a slide platform 1400 having the fingers 1410 with the friction pads 2000 approaches the ramp 1130 holding a slide 1000 at an angle. An approaching slide platform 1400 may trigger the cartridge 1100 to dispense a slide 1000, or a slide 1000 may be waiting for the platform 1400, as previously discussed.

The fingers 1410 are also spaced sufficiently close to each other so that they can pass between the ramp members 1130. As the fingers 1410 approach the slide 1000, the friction pads 2000 at the ends of the fingers 1410 engage the slide 1000 that is held on the ramp 1130 at an angle by the stop bumps 1910. The friction pads 2000 engage the end of the slide 1000 and, the end of the slide 1000 is raised above the stop bumps 1910. As a result, the slide 1000 is released from the ramp 1130, causing the slide to fall down onto the fingers 1410. The platform 1400 and the fingers 1410 having the slide 1000 thereon move past the ramp 1130. Another slide 1000 can then be dispensed from the cartridge 1100 and placed on the ramp 1130 for the next platform 1400 or for the next pass of the same platform.

Embodiments that stack slides horizontally on a side or partially on a side provide a number of benefits compared to conventional "vertically stacked" slides in a cartridge. For example, slides can be dispensed from a cartridge using gravity. Thus, vertical forces that are applied to individual slides, are eliminated or significantly reduced since slides rest on a bottom of a cartridge rather than being stacked on top of each other. As a result, the sizes of cartridges are no longer limited by the weight or number of slides that can be stacked on top of each other. Rather, cartridges can have various sizes to store various numbers of slides since the vertical weight of other slides above is no longer an issue. Thus, larger cartridges can be utilized, providing more efficient processing since cartridges can be replaced with less frequency, resulting in less downtime of processing equipment.

Embodiments provide additional benefits relating to the positioning slides. For example, slides are dispensed from a cartridge in a more consistent manner so that the slide can be predictably positioned and picked or selected by processing equipment. In contrast, slides that are dispensed from a bottom of a stack of slides can exhibit irregular motion while being dispensed. For example, the slides may "tidly wink" or flop up at an angle while being dispensed due to the force from the weight of the slides above being applied to an edge of the slide being pushed out from underneath the stack. Such irregular movements can result in slide placement and picking errors, and damage to slides. Embodiment eliminate these irregular motions, thus providing move reliable and accurate slide positioning.

Further, the ramp configuration provides more flexibility for processing equipment to select and pick the slide from the ramp. For example, in some systems, slide selection platforms are moved between different vertical positions to engage a slide that is presented at the bottom of a cartridge. With embodiments having a ramp, however, the slide is presented at a level where the selection platform or fingers extending there from can pass between the ramp members at a consistent vertical position to select and pick the slide from the end of the ramp members. In other words, a slide is presented to a picking mechanism in a desired position. Thus, it is not necessary to raise and lower slide platforms in order to access a slide, thus simplifying the programming and control and longevity of processing equipment. Additionally, embodiments simplify other related mechanical, electrical, software and control components since the slide is presented on a ramp in a consistent manner and easily accessible to a slide picking mechanism. Further, as necessary, the cartridge can be configured with a stop that closes the aperture in the bottom of the cartridge. When the cartridge is inserted into a processing system, the stop can be actuated to open the cartridge. Thus, when not in use, the stop allows the cartridge to be moved from place to place without slides falling out of the cartridge through the aperture.

Figure 23:
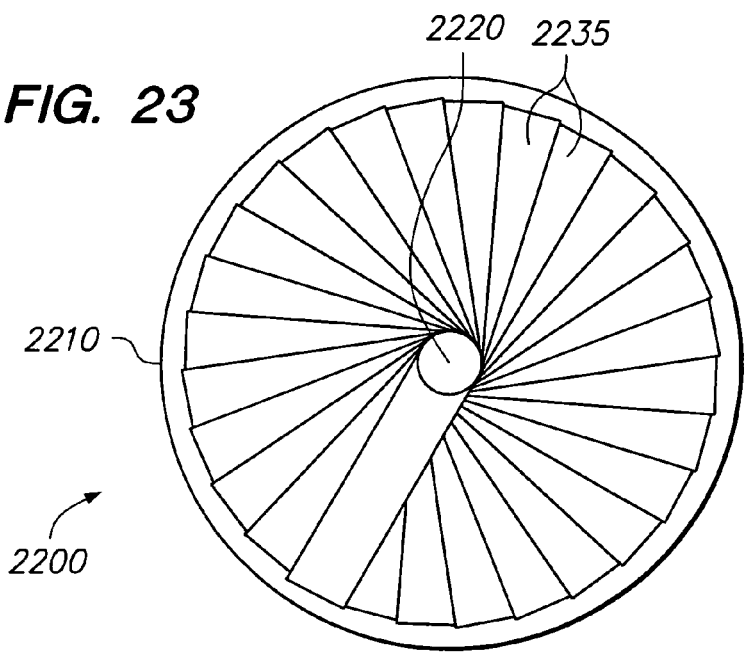
FIG. 23 is a top view of a cartridge having trays and slides that are arranged in a spiral or helical arrangement.

In a further embodiment, referring to FIGS. 22 and 23, a slide presentation module 2200 includes a cartridge or outer body 2210, a shaft 2220, trays 2230 that hold slides 2235, a drive mechanism 2240, such as a motor, and an actuator 2250. Trays 2230 are connected to the shaft 2220 and can hold a slide 2235 thereon. The drive mechanism 2240 is coupled to the shaft 2220 to rotate the shaft 2220 and the trays 2230 attached thereto. The actuator 2250 is activated so that the actuator 2240 displaces a slide 2235 that is initially at rest on a tray 2230, displacing the slide from an original position on the tray 2230 inside the cartridge 2210 to an extended position that is partially or completely outside of the cartridge 2210.

Figure 24A:
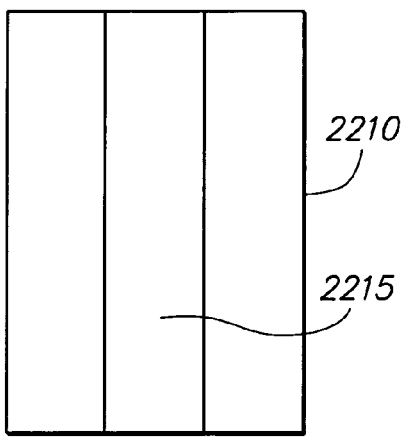
FIGS. 24A-B are respective side and top views of a cartridge having a vertical slot extending between the top and bottom of the cartridge for storing slides in a spiral or helical arrangement according to one embodiment.
Figure 24C:
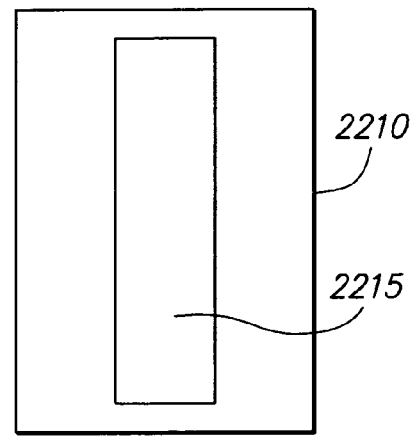
FIGS. 24C-D are respective side and top views of a cartridge having a slot extending partially between the top and bottom of the cartridge; for storing slides in a spiral arrangement according to another embodiment.
Figure 24B:
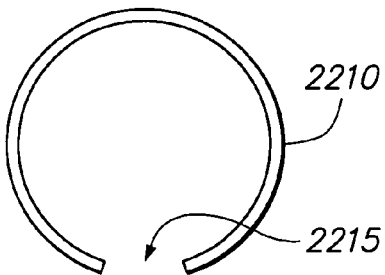
Figure 24D:
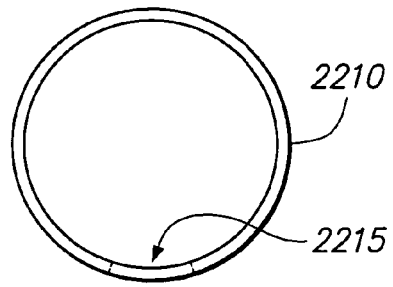

More particularly, referring to FIGS. 22-24D, in the illustrated embodiments, the cartridge 2210 has a circular shape and defines a vertical slot 2215. The slot 2215 has a width to allow a slide to pass through the slot 2215. The slot 2215 may extend for the entire height of the cartridge 2210 (as shown in FIGS. 24A-B) or for a portion of the height of the cartridge 2210 (as shown in FIGS. 24C-D). Persons skilled in the art will appreciate that the cartridge 2210 can have other shapes besides circular shapes and different slot 2215 configurations. Thus, embodiments shown with a circularly shaped cartridge 2210 are provided for explanation and illustration, not limitation.

The trays 2230 and the slides 2235 thereon wrap around the shaft 2220 and are arranged in a circular fanning, helical or spiral staircase type arrangement. Slides 2235 can be initially loaded onto a circular or fanning arrangement of trays 2230 by arranging the slides 2235 as a vertical stack (one on top of another), and rotating radially and vertically offset trays 2230 into the stack of slides 2235 so that a slide 2235 is placed on each tray 2230 as the trays 2230 are rotated. As a result, it is not necessary for a cytotechnologist to manually place a slide on each tray. Rather, the slides can be placed onto respective trays in a semi-automated manner by rotating the trays and forcing a slide onto each tray. Thus, in one embodiment having 120 trays 2230, 120 slides 2235 can be placed onto respective trays 2230, and each tray 2230 and slide 2235 are radially and vertically displaced from an adjacent tray 2230 and slide 2235.

More specifically, as shown in FIGS. 22 and 23, each tray 2230 is radially and vertically offset from an adjacent tray 2230, i.e., a tray above a subject tray and a tray below a subject tray. The amount of the radial offset and vertical offset can vary depending on the number of trays 2230 and other design considerations.

For example, with a cartridge 2210 and a shaft 2220 capable of storing and holding 120 trays and 120 slides, the radial offset of one tray 2230 from an adjacent tray 2230 can be determined by calculating (360 degrees/# of trays). In the example with 120 trays 2230, each tray 2230 can be offset from an adjacent tray 2230 by 3 degrees. For example, with 60 trays, the offset can be 360 degrees/60 trays=6 degrees. Indeed, other radial offsets may be used with different numbers of trays 2230. Thus, an offset of 3 degrees for 120 trays is merely provided as one exemplary radial offset. The vertical offset can be, for example, about 0.041" to about 0.051", and can vary depending on, for example, the design and height of the cartridge 2210, the height and number of the trays 2230, and the size of the shaft 2220.

Figure 25:
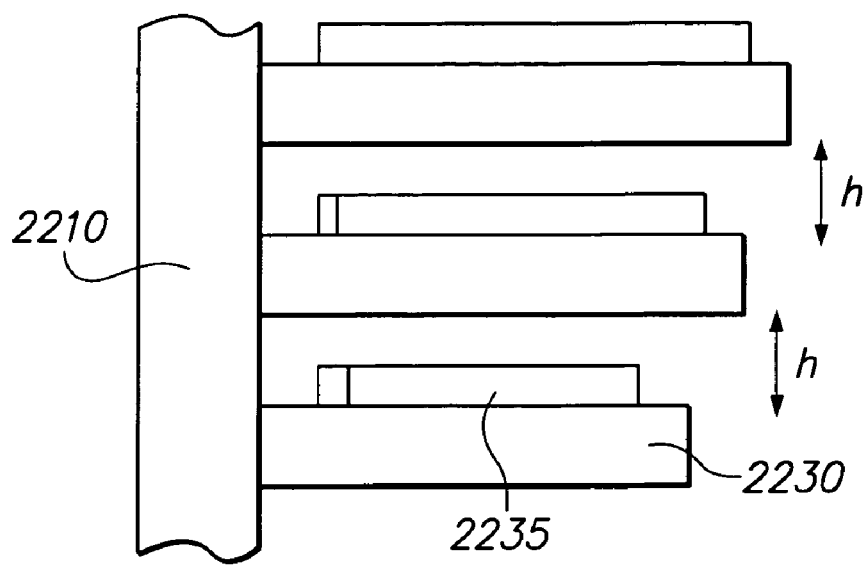
FIG. 25 is an exploded side view of trays supporting slides.
Figure 26:
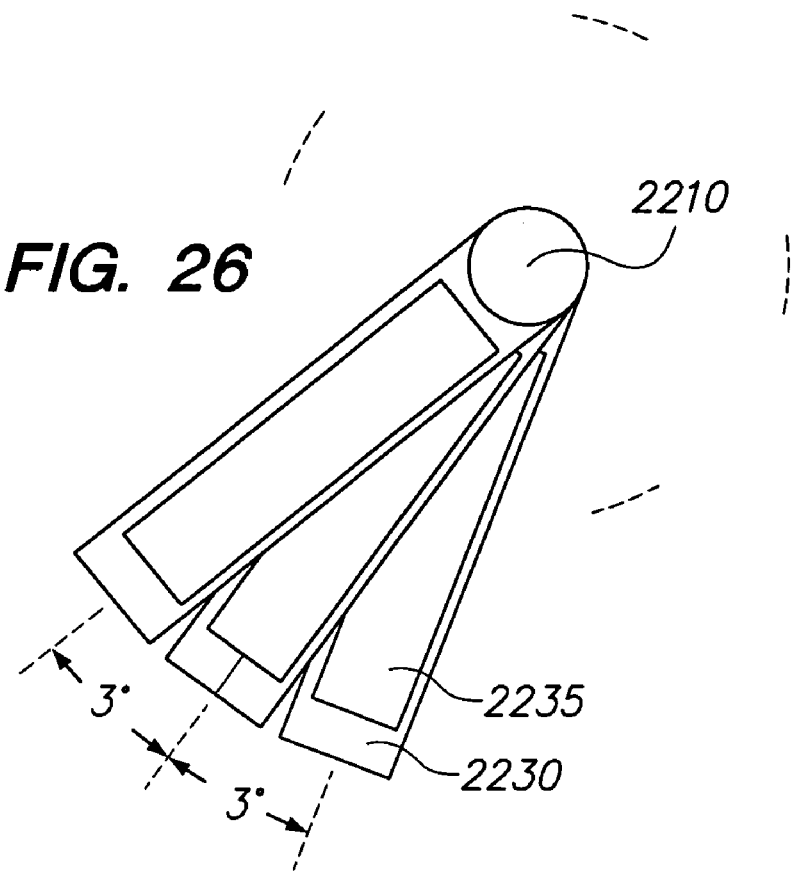
FIG. 26 is an exploded top view of trays supporting slides.

In one embodiment, as shown in further detail in FIGS. 25 and 26, each tray 2230 is radially and vertically offset from an adjacent tray 2230 by approximately the same number of degrees and the same height. Further, in the illustrated embodiment, all of the trays 2230 are approximately the same length, and thus, extend from the central shaft 2220 for about the same distance. This configuration may be advantageous so that a the shaft can be rotated a consistent number of degrees to position the next tray and next slide to be processed. Persons skilled in the art will appreciate that other configurations can also be utilized, and it is not necessary that the radial and vertical offsets of the trays 2230 and slides 2235 necessarily be the same.

The motor 2240 rotates the shaft 2220, thus rotating the trays 2230 and slides 2235 thereon around the shaft 2220. The motor 2240 can rotate the shaft 2220 in a stepwise or intermittent manner (e.g. 3 degrees per step) so that a tray 2230 and a slide 2235 are positioned adjacent to the slot 2215 after each step.

Figure 27:
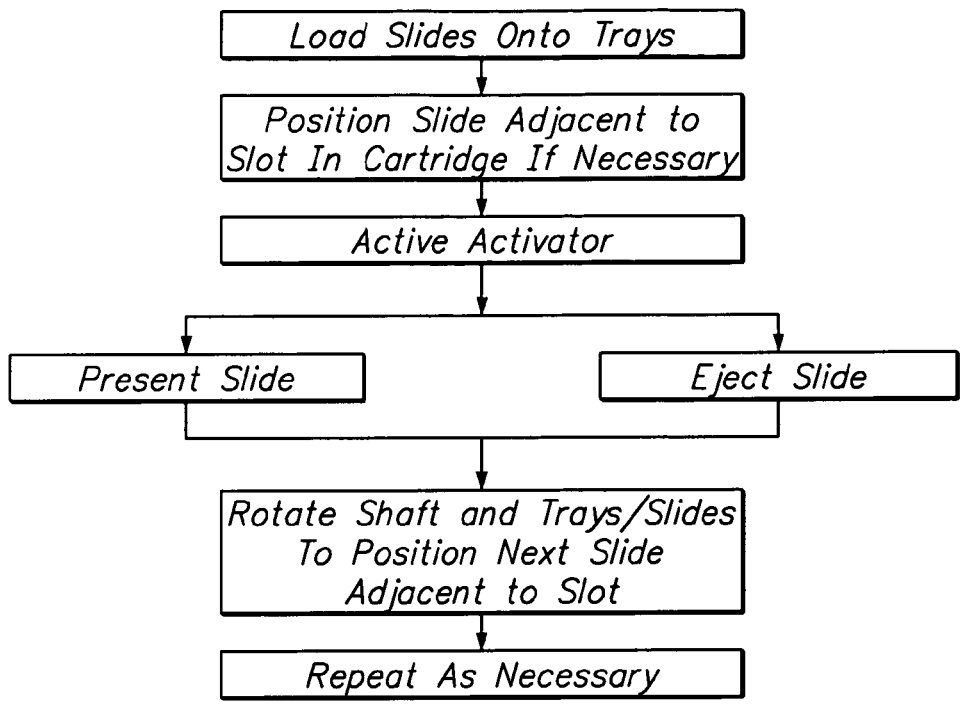
FIG. 27 is a flow chart illustrating loading into and dispensing slides from a cartridge according to one embodiment.
Figure 28:
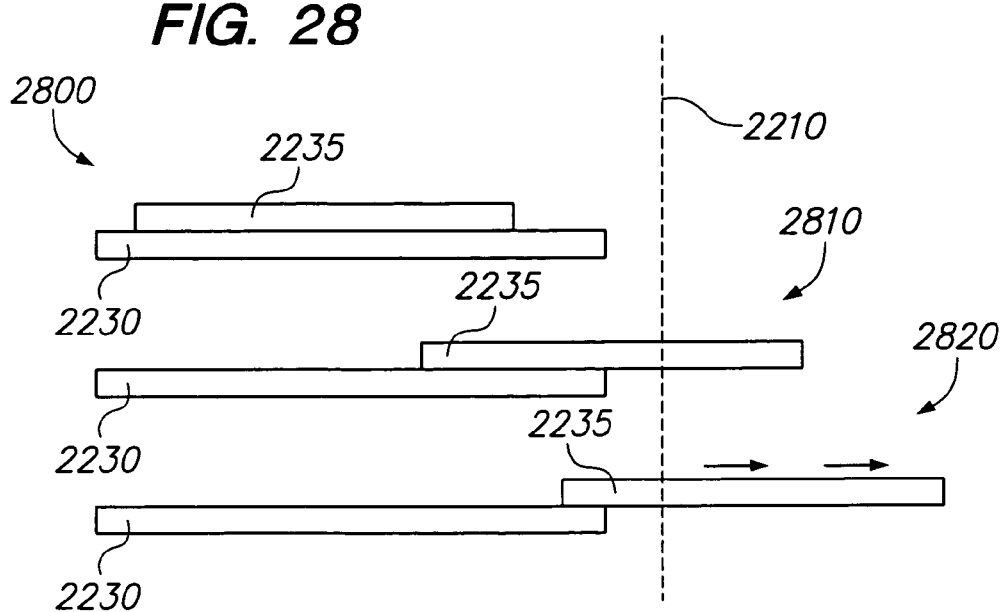
FIG. 28 illustrates an original position of a slide on a tray and extended positions.

In use, referring to FIG. 27, in step 2700, slides are initially loaded onto trays. For example, as previously discussed, slides 2235 can be loaded onto a circular or fanning arrangement of trays 2230 by arranging the slides 2235 in a stack, and rotating radially and vertically offset trays 2230 into the stack of slides 2235 so that a slide 2235 is placed on each tray 2230.

In step 2710, a first tray and a first slide thereon are initially positioned at the slot of the cartridge. The first tray and first slide may be so positioned with or without activation of the motor to rotate the shaft depending on how the trays with slides are initially arranged in the cartridge 2210.

In step 2720, an actuator is activated to contact the next or top available slide. As a result, the slide is displaced from its original position on the first tray to an extended position. In step 2730, a cytotechnologist, a robotic device, or another slide processing station can retrieve and remove the slide in the extended position from its tray.

The extended position can be a slide being a first slide 2235 is displaced from an initial position 2800 to an extended position, which can be a presentation position 2810 or an ejected position 2820. In the presentation position 2810, in the absence of any vertical supports (beyond that, as in this example, supplied by the friction wheel 2900 of actuator 2250 as shown in FIG. 29), at least half of the presented first slide should remain on the tray for purposes of balance and stability. In the presentation position, the first slide is displaced along the first tray and remains on the first tray. One end of the first slide extends partially outside of the cartridge 2210 through the slot so that the first slide can be handled or grabbed by a cytotechnologist.

Alternatively, a slide 2235 can be displaced from an initial position 2800 to an ejected position 2820. In the ejected position, the actuator can displace the first slide completely off of the first tray and out of the cartridge through the slot and onto, for example, another piece of slide processing equipment or a conveyor system.

Various actuators can be used to displace a slide from an initial position to an extended position. For example, the actuator can be a manual actuator, such as a switch or lever, that is activated by a cytotechnologist to present or eject a slide from the cartridge. The actuator can also be a friction wheel 2900, as shown in FIG. 29. An outer circumferential surface 2910 of the friction wheel 2900 contacts a top surface of the slide. The friction wheel 2900 rotates at a sufficient speed to at least partially displace a slide from the original position on the tray from the original position to the extended position when the friction wheel 2900 contacts a slide. Alternatively, as shown in FIG. 30, the actuator can be a reciprocating member 3000 that moves back and forth and engages an edge of a slide to displace the slide from its initial position to an extended position.

Referring again to FIG. 27, in step 2740, the motor rotates the shaft so that a second tray having a second slide is rotated into a position adjacent to the slot, thus assuming the previous position of the first tray, which is now empty. In the example provided, the motor can rotate the shaft 3 degrees, to place the second tray and second slide adjacent to the slot.

In step 2750, an actuator is activated to contact the second slide. As a result, the second slide is displaced from its original position on the second tray to an extended position. In step 2760, a cytotechnologist, a robotic device, or another slide processing station can retrieve and remove the slide from its tray in the extended position. The process repeats, as necessary to present or eject additional slides for third, fourth and subsequent slides rotating the shaft in a stepwise manner, e.g., 3 degrees per step, to position the next tray and slide adjacent to the slot.

In one embodiment, the slides are rotated and raised up to the actuation member 2250 such as a friction wheel. For example, the trays 2230 may be rotated so that the empty trays are indexed above the actuation member 2250, and the next slide to be displaced is positioned so that the actuator 2250 can displace the slide to the extended position. Alternatively, the actuator 2250, can be indexed downward to the next slide that is positioned adjacent tot the slot 2215. Persons skilled in the art will appreciate that different indexing and rotational configurations can be used with different cartridge designs.

Embodiments provide an apparatus and an effective manner of presenting or removing slides from a cartridge while eliminating the vertical forces that otherwise result when slides are stacked one on top of another in a cartridge. Thus, the slides are reliably positioned as needed, without irregular movements that may otherwise occur as a result of uneven vertical forces being applied to edges of slides when slides are stacked on top of each other.

Although references have been made in the foregoing description to various embodiments, persons skilled in the art will recognize that insubstantial modifications, alterations, and substitutions can be made to the described embodiments without departing from embodiments as claimed.

What is claimed is:

1. A system for processing a specimen vial, comprising:
   a first member configured for holding a vial, the first member rotatable about a first axis for moving a held vial from a first location to a second location;
   a second member having a capping mechanism configured for removing and re-attaching a cap of a vial held by the first member, the second member rotatable about a second axis for positioning the capping mechanism proximate the first location for removing a cap of a vial held by the first member at the first location, and proximate the second location for re-attaching the cap to the vial held by the first member at the second location.

2. The system of claim 1, wherein the capping mechanism is configured for retaining a removed cap until it is re-attached to the vial.

3. The system of claim 1, wherein the first and second axes are substantially aligned.

4. The system of claim 3, wherein the second member rotates above the first member.

5. The system of claim 1, wherein the first and second axes are substantially parallel.

6. The system of claim 5, wherein the second member rotates above the first member.

7. A system for processing a specimen vial, comprising:
   a first member configured for loading, holding and unloading a vial, the first member rotatable about a first axis for positioning a held vial at each of first, second and third locations;
   a second member having a capping mechanism configured for removing and re-attaching a cap of a vial held by the first member, the second member rotatable about a second axis for positioning the capping mechanism proximate the first location for removing a cap of a vial held by the first member at the first location, and proximate the third location for re-attaching the cap to the vial held by the first member at the third location.

8. The system of claim 7, wherein the capping mechanism is configured for retaining a removed cap until it is re-attached to the vial.

9. The system of claim 7, wherein the first location is a vial loading and uncapping location, the second location is a presentation location, and the third location is a re-capping and unloading location.

10. The system of claim 7, the first member having a plurality of lobes, each lobe configured for receiving and holding a respective vial.

11. The system of claim 10, the first member having three lobes arranged in a triangular configuration.

12. The system of claim 7, the second member having a plurality of lobes, each comprising a capping mechanism configured for removing and re-attaching a cap of a vial held by the first member.

13. The system of claim 7,
   the first member having three lobes arranged in a triangular configuration, each lobe configured for receiving and holding a respective vial, and
   the second member having two lobes, each comprising a capping mechanism configured for removing and re-attaching a cap of a vial held by a lobe of the first member.

* * * * *